(12) United States Patent
Yeung et al.

(10) Patent No.: US 8,105,344 B2
(45) Date of Patent: Jan. 31, 2012

(54) SPOOLED FILAMENT TO REPAIR TISSUE

(75) Inventors: Jeffrey E. Yeung, San Jose, CA (US);
Teresa T. Yeung, San Jose, CA (US)

(73) Assignee: Aleeva Medical Inc., San Jose, CA (US)

( * ) Notice: Subject to any disclaimer, the term of this patent is extended or adjusted under 35 U.S.C. 154(b) by 570 days.

(21) Appl. No.: 12/309,148

(22) PCT Filed: Jul. 25, 2007

(86) PCT No.: PCT/US2007/016763
§ 371 (c)(1),
(2), (4) Date: Jan. 8, 2009

(87) PCT Pub. No.: WO2008/013869
PCT Pub. Date: Jan. 31, 2008

(65) Prior Publication Data
US 2010/0030241 A1     Feb. 4, 2010

(51) Int. Cl.
*A61B 17/04* (2006.01)

(52) U.S. Cl. .................. 606/145; 606/144

(58) Field of Classification Search .............. 606/148, 606/139, 144–146, 191, 222–233
See application file for complete search history.

(56) References Cited

U.S. PATENT DOCUMENTS

| 5,649,939 | A | * | 7/1997 | Reddick | 606/148 |
| 6,053,899 | A | * | 4/2000 | Slanda et al. | 604/500 |
| 7,833,281 | B2 | * | 11/2010 | Lehman et al. | 623/23.7 |

* cited by examiner

*Primary Examiner* — Darwin Erezo
*Assistant Examiner* — Gregory Anderson
(74) *Attorney, Agent, or Firm* — Carol Titus; GSS Law Group

(57) ABSTRACT

A filament-guiding device directs a filament to spool over a rotating device within tissue. The filament-guiding device has both closed and open positions. In the closed position, the filament-guiding device is resiliently straightened for delivering into tissue. Within tissue, the filament-guiding device resumes a curved configuration in the open position to orient the filament perpendicular to the rotating device for spooling. The spooled filament is deployed by withdrawing the rotating device and filament-guiding device to bulk and repair the tissue.

31 Claims, 38 Drawing Sheets

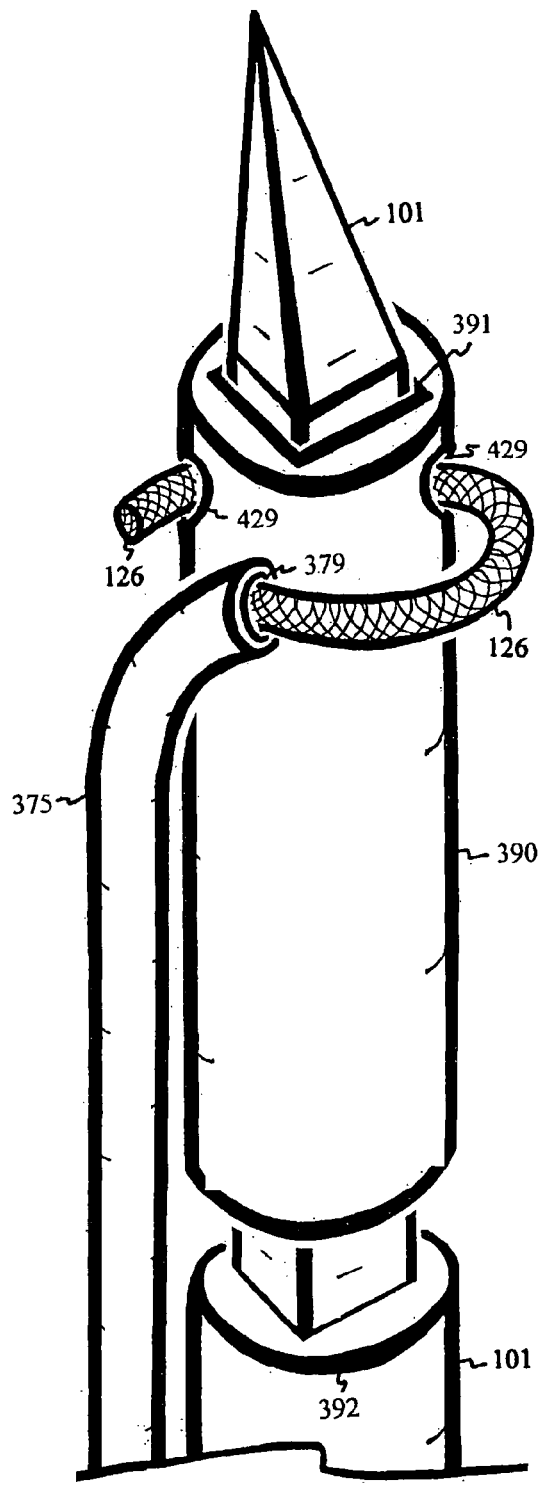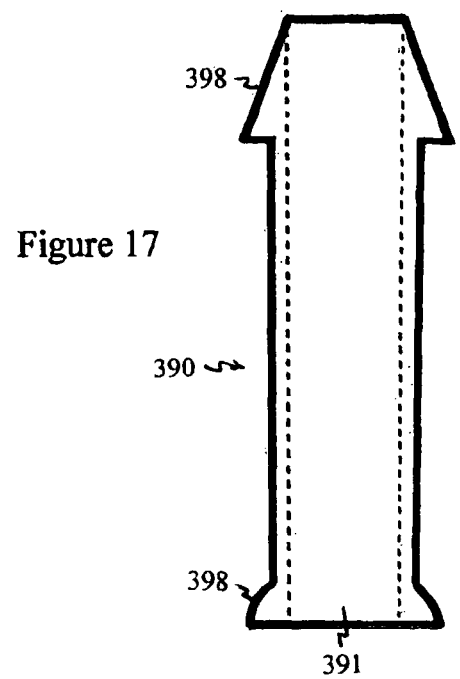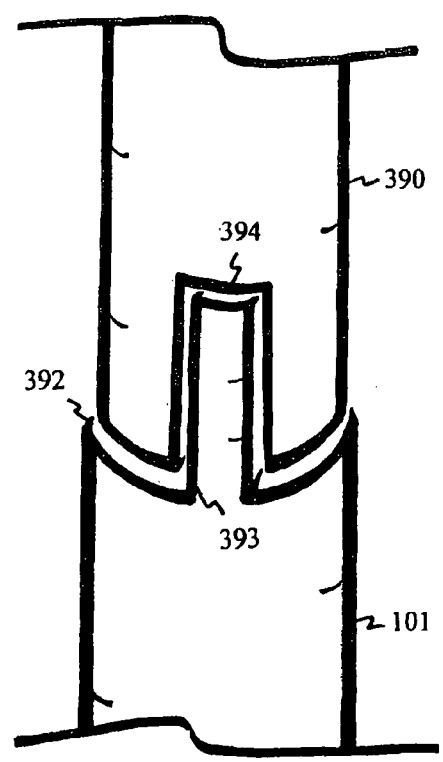
Figure 16
Figure 17
Figure 18

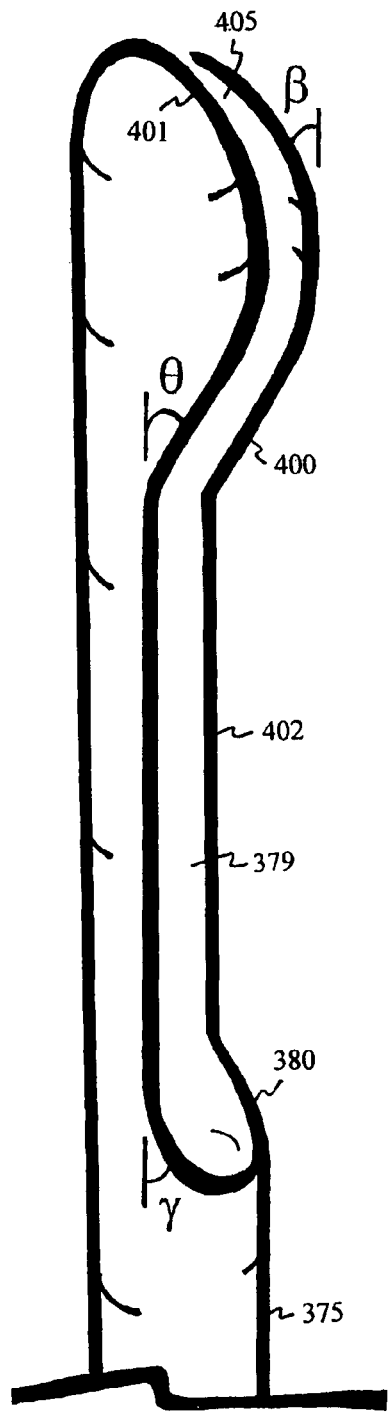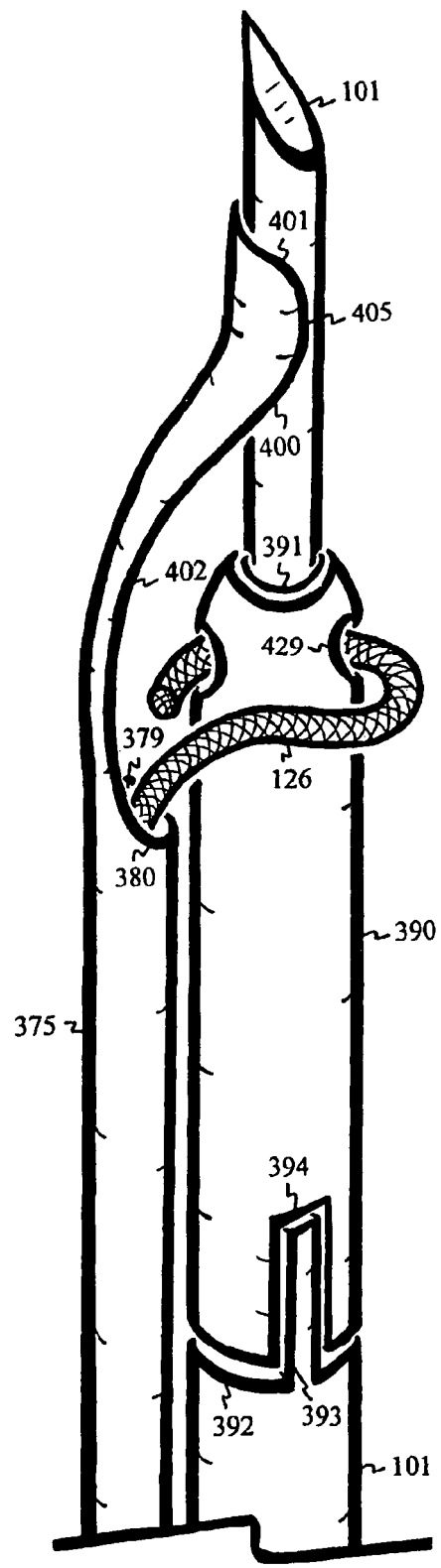
Figure 19
Figure 20

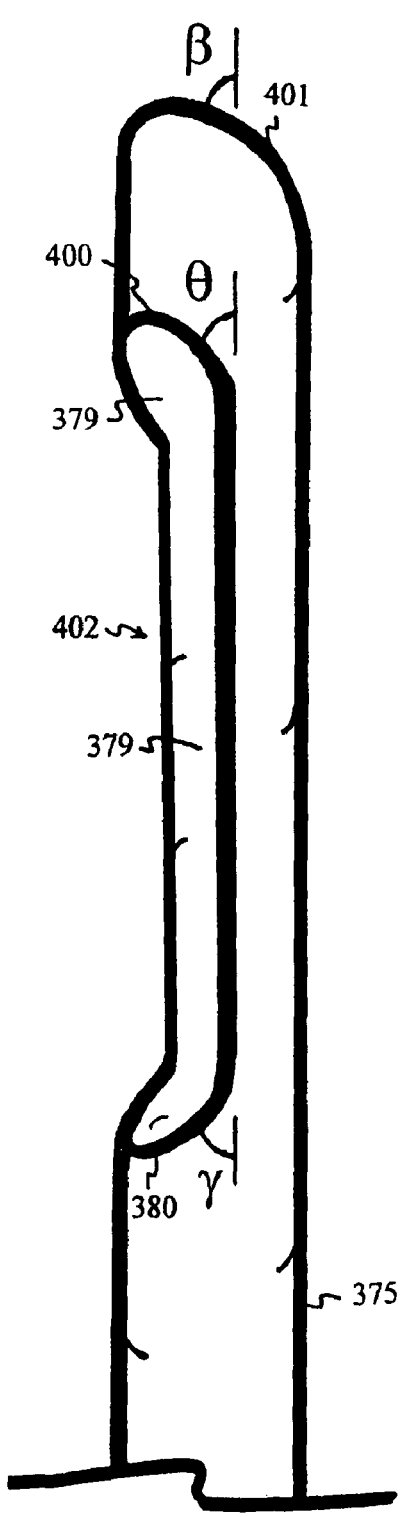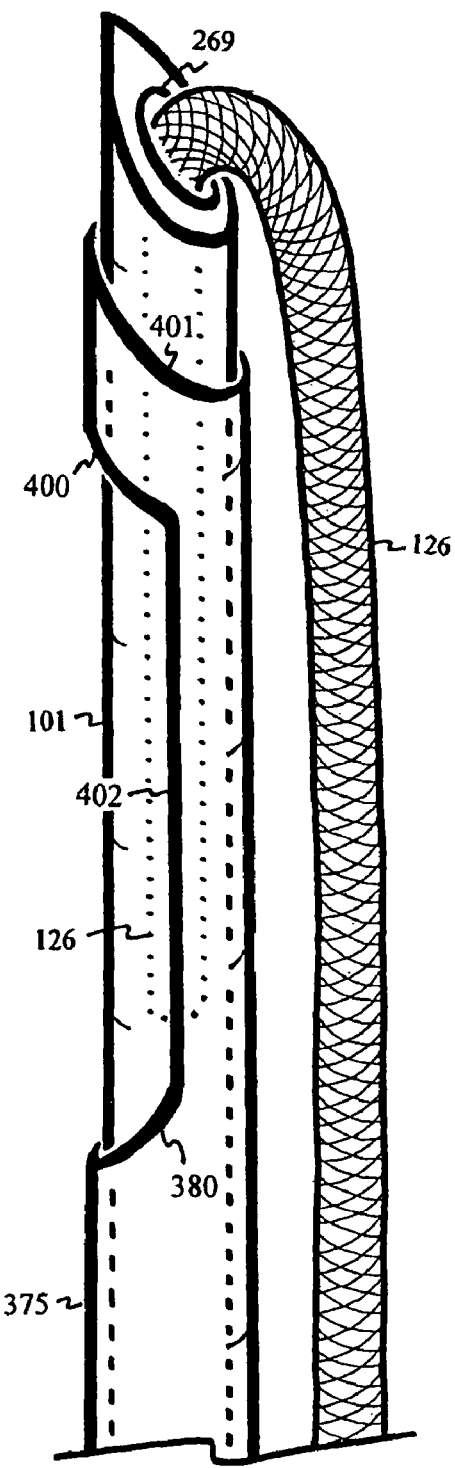
Figure 21
Figure 22

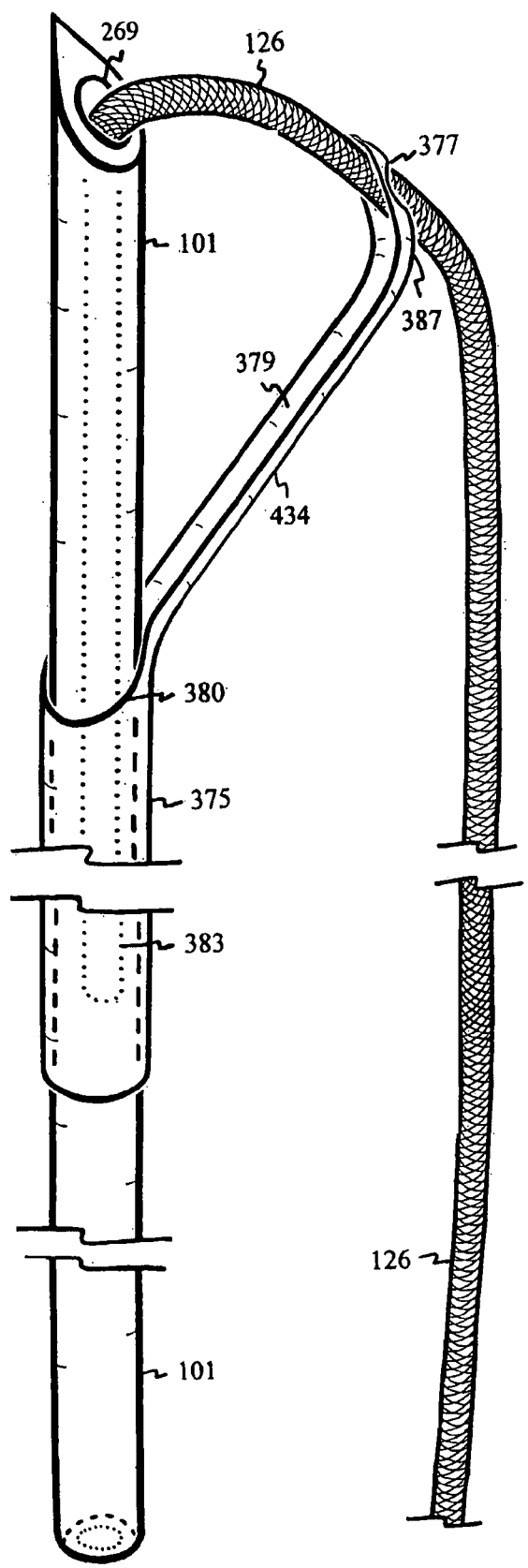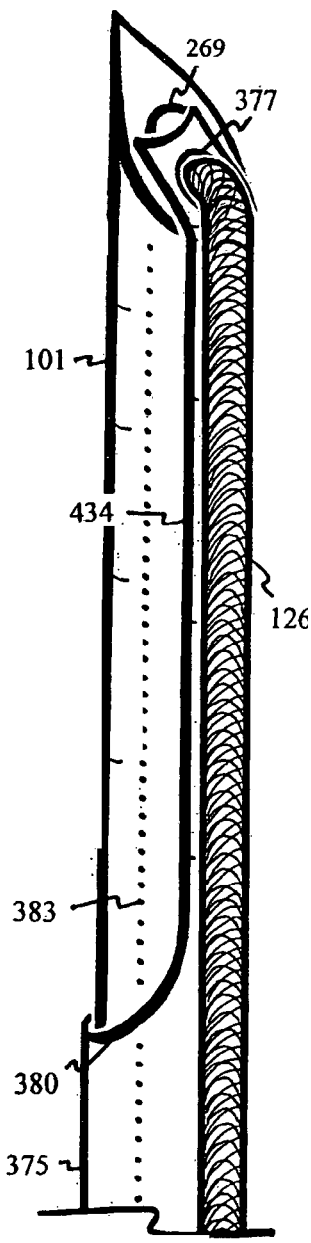
Figure 37
Figure 38

SPOOLED FILAMENT TO REPAIR TISSUE

FIELD OF INVENTION

This invention relates to a device for spooling a biocompatible filament into a ball or cylinder to bulk, fill, support or repair defective tissue.

BACKGROUND

Due to aging and multiple factors, supportive tissue degenerates. As a result, tissue malfunctions or causes pain. For example, an unsupported urethra leads to urinary stress incontinence. Degenerated intervertebral discs shift compressive loads to facet joints, causing strain and pain. Osteoporotic loss of bone matrix leads to collapse of the vertebral body, causing deformity and pain. In cosmetics, unsupported junctions between muscles form wrinkles. Acne causes the loss of epidermis and forms pits beneath the skin.

Injection of bulking agents, such as collagen, hyaluronate, polyethylene glycol, silicon particles, glass particles, Teflon particles and polyurethane particles, have been used or proposed to correct unsupported tissue of various kinds; but injections of these gel or particles can migrate or be metabolized or oxidized over time.

SUMMARY OF INVENTION

A spooled filament can bulk and restore function or appearance of some degenerated tissues through a needle puncture. A spooling apparatus contains a rotating device, filament and filament-guiding device, all within a tissue-puncturing needle. The filament-guiding device has a closed and open position. The closed position is used during tissue puncturing; the open position is for filament spooling within degenerated tissue. The filament-guiding device is increasingly elastic toward the distal end, forming increasingly tight curvatures. To spool over the rotating device, the distal end of the filament-guiding device orients the filament from its parallel tissue entry position to the perpendicular spooling position. The rotating device, filament-guiding device and tissue-puncturing needle are then withdrawn to deploy the spooled filament, thereby bulking and repairing the degenerated tissue.

REFERENCE NUMBER

100 Intervertebral disc
101 Rotating needle
105 Cartilaginous endplate
113 Mucosa
114 Vagina
115 Pubis
123 Spinal cord
126 Filament, string, wire or thread
128 Nucleus pulposus
129 Facet joint
150 Urethral lumen
151 Posterior wall of urethra
152 Anterior wall of urethra
159 Vertebral body
194 Nerve root
269 Lumen of the rotating needle
278 Pedicle
375 Elastic tube
377 Hole of the extension arm
379 Lumen of the elastic tube
380 Proximal wall of the window
381 Introducer needle
382 Lumen of the introducer needle
383 The filament within the rotating needle
385 Punctured hole
386 Annular layers
387 Bend of the elastic extension arm
388 Slit of the rotating needle
389 Open slit of the hole of the elastic extension arm
390 Spindle, bobbin or reel
391 Lumen of the spindle
392 Step of the rotating needle
393 Protrusion
394 Indentation
395 Protrusion of the filament
396 Indentation of the filament
397 Urethra
398 Tapered edge of the spindle
399 Indentation of the taper edge
400 Distal wall of the window
401 Distal end of the elastic tube
402 Window of the elastic tube
404 Acne scar or tissue
405 Groove of the elastic tube
429 Channel in the spindle for filament
430 Lumen separator
431 A first lumen of the introducer needle
432 A second lumen of the introducer needle
433 Compressed vertebral body
434 Elastic extension arm
435 Elastic extension tube
436 Tapered end of extension arm
437 Beveled tip of extension tube
438 Slot or opening on the extension arm
439 Sharp tip of the introducer needle

DESCRIPTION OF THE DRAWINGS

FIG. 16 shows the rotating needle 101 sharpened for tissue 404 puncturing capability.

FIG. 17 shows the tapered edges 398 at distal and proximal ends of the spindle 390.

FIG. 18 shows tongue and groove rotational engagement using a protrusion 393 from the rotating needle 101 and an indentation 394 in the spindle 390.

FIG. 19 shows a window 402 and a groove 405 at the distal end of the elastically straightened tube 375.

FIG. 20 shows connection between the elastic tube 375 and rotating needle 101 with tissue puncturing and filament 126 spooling capability.

FIG. 21 shows a window 402 at the distal portion of the elastically straightened tube 375.

FIG. 22 shows the closed position of the elastic tube 375 resiliently straightened by the rotating needle 101 which houses a portion of the filament 126 in its lumen 269.

FIG. 37 shows the filament 126 extending into the lumen 269 of the rotating needle 101.

FIG. 38 shows the closed position of the elastic extension arm 434 with the filament 126 ready for tissue puncturing and spooling.

DETAILED DESCRIPTION OF THE EMBODIMENTS

Figure 1:
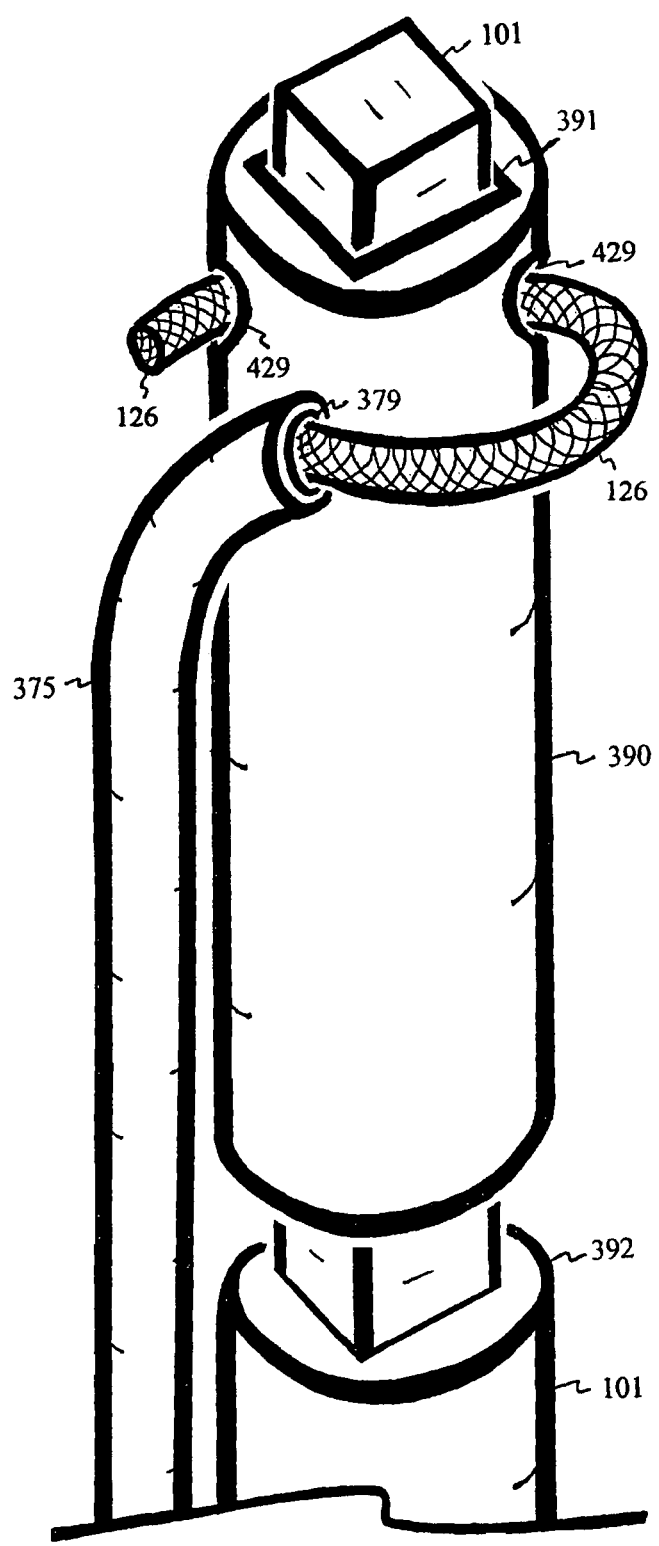
FIG. 1 shows a filament 126 extending from an elastically curved tube 375 and attaching to a spindle 390 over a blunt rotating needle 101 with a step 392.

For micro-invasive tissue bulking using spooled filament, both the filament 126 and a rotating device enter into tissue parallel to each other through a small puncture. The filament 126 guiding device has a closed position for tissue insertion and an open position for filament 126 spooling. In the open position, the guiding device orients the filament 126 for spooling over the rotating device. Orientation for filament 126 spooling is approximately 90° or perpendicular to the direction of tissue entry by the filament 126.

Orientation of the filament 126 from parallel to perpendicular requires shape change of the filament 126 guiding device within the tissue. The shape change within tissue is preferred to occur within a small space to minimize tissue damage. The filament guiding device also allows size of the spooled filament 126 to increase. After spooling, both the filament guiding and rotating devices are withdrawn to deploy the spool of filament 126 to bulk, support or repair the tissue.

The guiding device is elastic or has shape memory to hold a closed position for tissue insertion or an open position for filament 126 spooling. The guiding device can be an elastic tube 375, which can be further modified with an extension arm 434 or connected to an elastic extension tube 435.

The rotating device can be a rotating needle 101 and/or a spindle 390 for spooling the filament 126 directed by the guiding device. The rotating and the guiding devices can be connected or combined, forming a tissue puncturing and filament guiding device. The rotating and guiding devices can also be delivered within an introducer needle 381 into tissue.

FIG. 1 shows a filament 126 extending from the lumen 379 of an elastically curved tube 375 through the channel 429 of a spindle 390 for attachment. The elastically curved tube 375 is the filament guiding device in the open position directing the filament 126 to the spindle 390 for spooling. Curvature of the elastic tube 375 orients or aligns the filament 126 approximately perpendicular to the rotating spindle 390 for spooling. The elasticity of the tube 375 allows the spool of filament 126 to expand in size by bending away while still directing the filament 126 over the growing spool.

The non-round cross-section of the lumen 391 of the spindle 390 is sized and configured to fit over a blunt rotating needle 101. The filament 126 traverses through the lumen 391 and provides gripping friction between the spindle 390 and the blunt rotating needle 101. The blunt rotating needle 101 has a step 392 to keep the spindle 390 at the distal end of the rotating needle 101.

Figure 2:
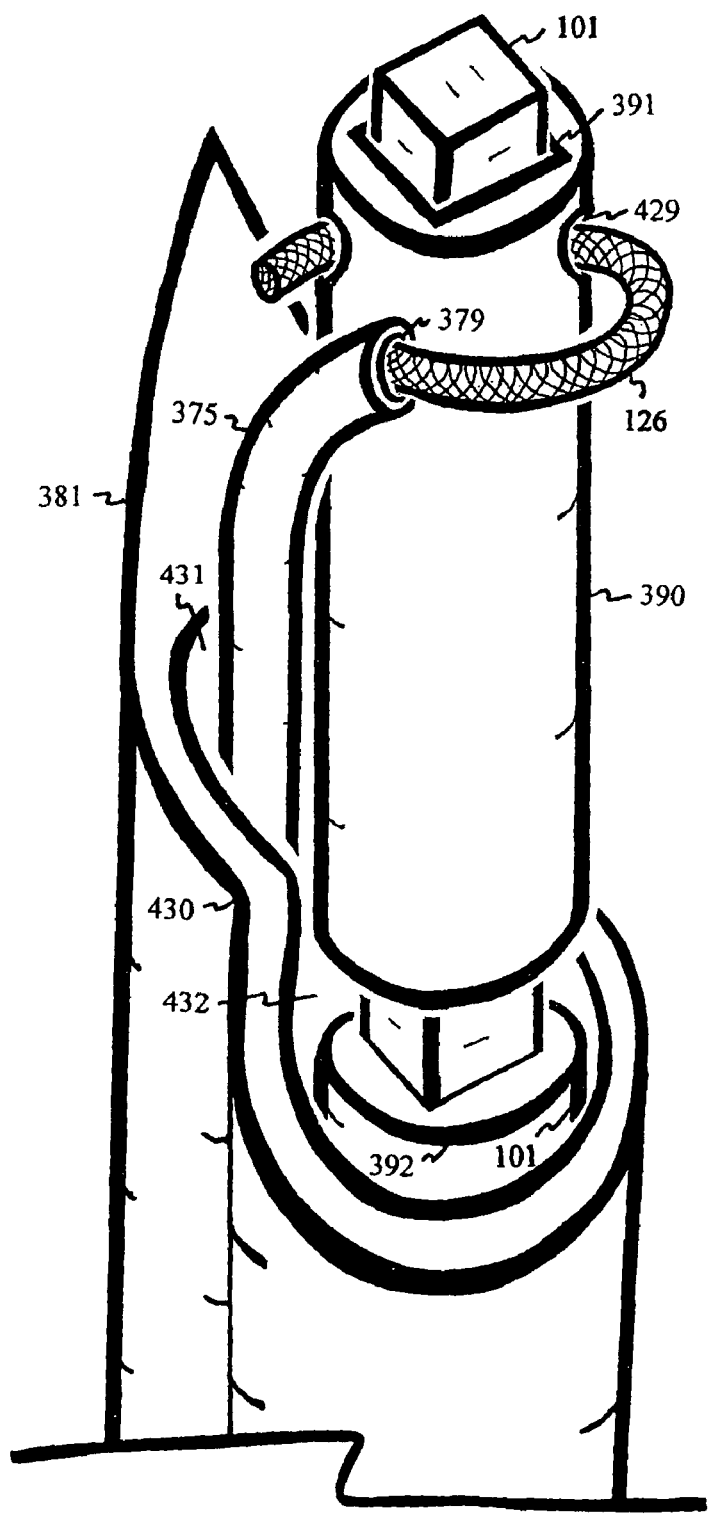
FIG. 2 shows both the elastically curved tube 375 and blunt rotating needle 101 within an introducer needle 381. The elastic tube 375 is within a first lumen 431, and the spindle 390 is within a second lumen 432.

The cross-section of the lumen of the introducer needle 381 can be oval, elongated crimped in the middle or irregular to fit both the elastically curved tube 375 and spindle 390, as shown in FIG. 2. The cross-section of the lumen of the introducer needle 381 can also be partially divided into the first lumen 431 and the second lumen 432, as shown in FIG. 2, or completely separated lumens. The first lumen 431 is near the long beveled tip of the introducer needle 381. The lumen separator 430 can be positioned between the first lumen 431 and the second lumen 432.

The elastically curved tube 375 is housed within the first lumen 431; the rotating needle 101 and spindle 390 are housed within the second lumen 432. The curvature of the elastic tube 375 guides, aligns and directs the filament 126 to about 90°, or perpendicular, from tissue entry to the spindle 390. As the blunt rotating needle 101 rotates, the filament 126 guided by the elastically curved tube 375 begins to spool over the spindle 390. Spooling of the filament 126 over the spindle 390 also pulls and tugs the elastically curved tube 375. The lumen separator 430 of the introducer needle 381, as shown in FIG. 2, anchors, holds, supports, stabilizes or separates the elastically curved tube 375 to prevent the elastic tube 375 from being pulled or wrapping around the rotating spindle 390.

Figure 3:
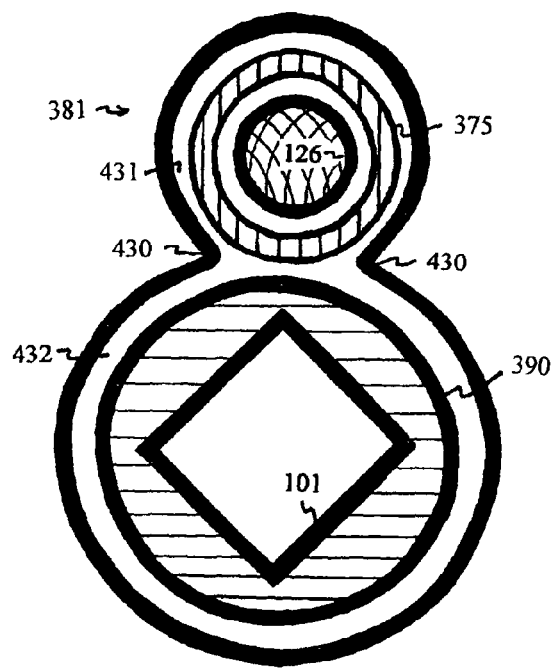
FIG. 3 shows a cross-section of the introducer needle 381, the elastically curved tube 375 and filament 126 within the first lumen 431, and the spindle 390 and rotating needle 101 within the second lumen 432.

The cross-section of the introducer needle 381 can be round or non-round, such as a figure eight configuration, as shown in FIG. 3. The first lumen 431 is sized and configured to house the elastically curved tube 375. The second lumen 432 is sized and configured to house the spindle 390 and rotating needle 101. The first lumen 431 and the second lumen 432 are partially or completely divided by lumen separators 430. The opening between the lumen separators 430 is smaller than the diameter of the elastically curved tube 375. The separators 430 prevent the elastically curved tube 375 from wrapping or spooling over the rotating device.

Figure 4:
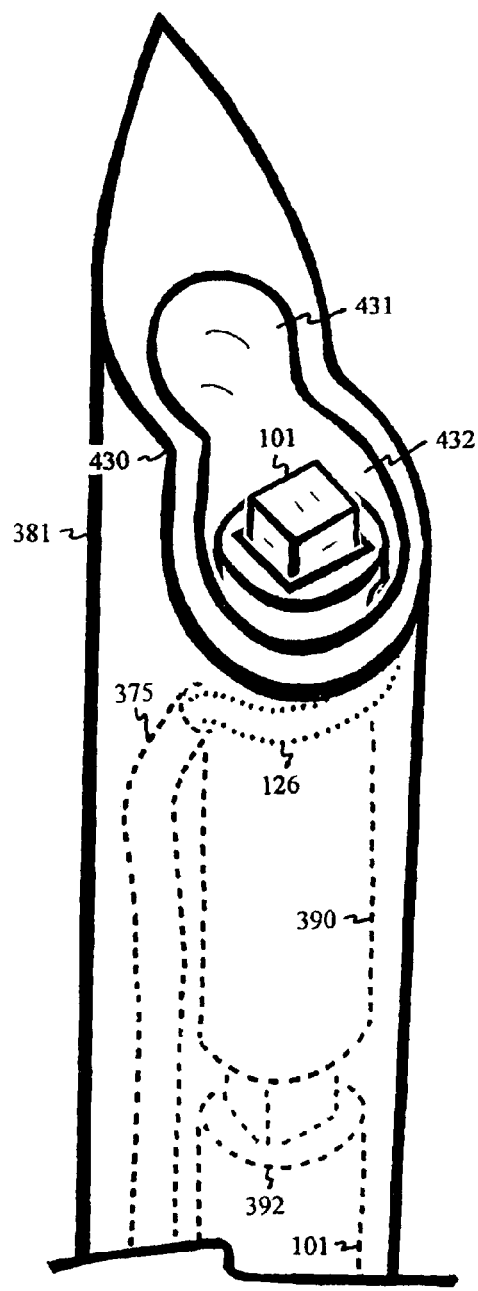
FIG. 4 shows the elastically curved tube 375 resiliently straightened in a closed position within the first lumen 431 and the spindle 390 within the second lumen 432.

The elastically curved tube 375 can be resiliently straightened in a closed position within the first lumen 431, as shown in FIG. 4, to minimize the size of the first lumen 431. The elastically curved tube 375 can be made with super-elastic or shape memory material, such as nickel-titanium alloy. The elastically curved tube 375 can also be made with elastic polymeric material. During spooling, the tension on the spooling filament 126 is sufficient to bend and curve the flexible or elastic tube 375.

Figure 5:
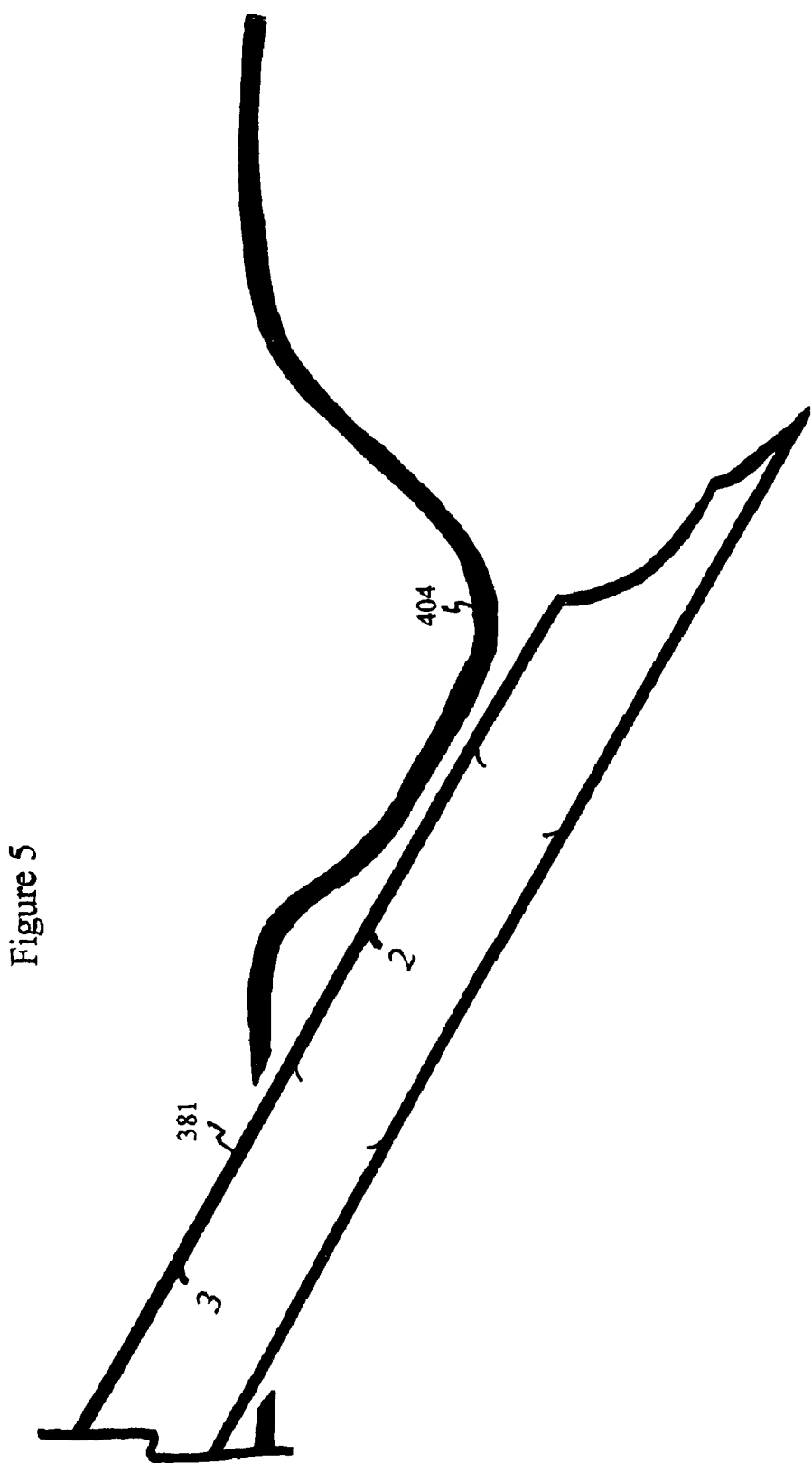
FIG. 5 shows the introducer needle 381 assembly in FIG. 4 punctured beneath an acne scar 404 or tissue.
Figure 6:
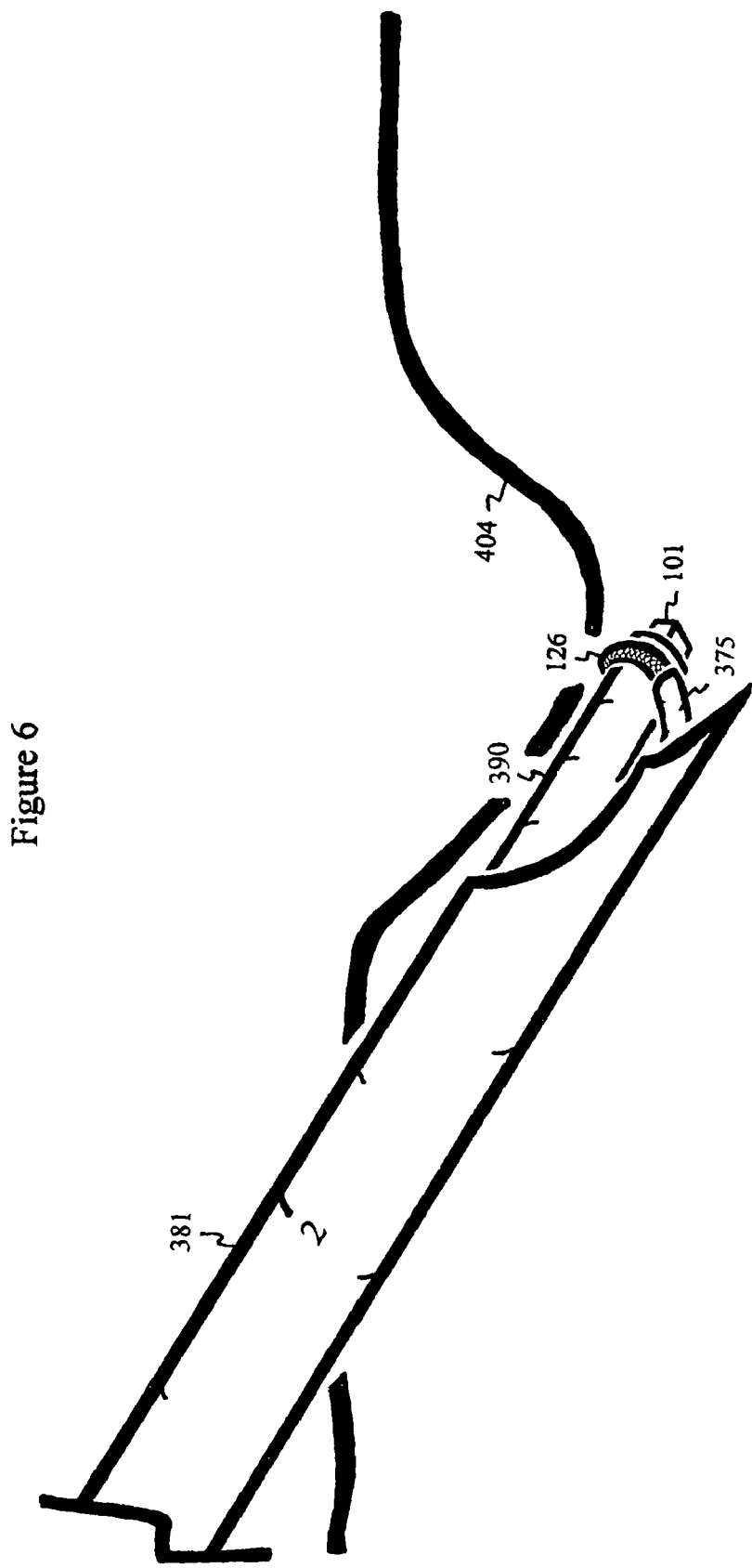
FIG. 6 shows partial withdrawal of the introducer needle 381 while stationarily holding and exposing the elastically curved tube 375, blunt rotating needle 101 and spindle 390.

The assembly of introducer needle 381, elastic tube 375, blunt rotating needle 101 and filament 126 is punctured beneath an unsupported tissue, pitted tissue or acne scar 404, as shown in FIG. 5. The introducer needle 381 can have penetration markers showing depth of puncture. The introducer needle 381 is partially withdrawn while holding and exposing the elastically curved tube 375, blunt rotating needle 101 and spindle 390, as shown in FIG. 6.

A significant proximal portion of the filament 126 is packaged within a transparent container located external to the patient. Drawing of the filament 126 from the transparent container for spooling is visible to the physician or operator during the spooling process. The physician or operator can also cut the filament 126 between the transparent container and the distal lumen 379 opening of the elastic tube 375, to limit the size of the spooled filament 126. The filament 126, interior of the transparent container, elastic tube 375, spindle 390, rotating needle 101 and introducer needle 381 are sterile with low bio burden to prevent infection and tissue reaction.

Figure 7:
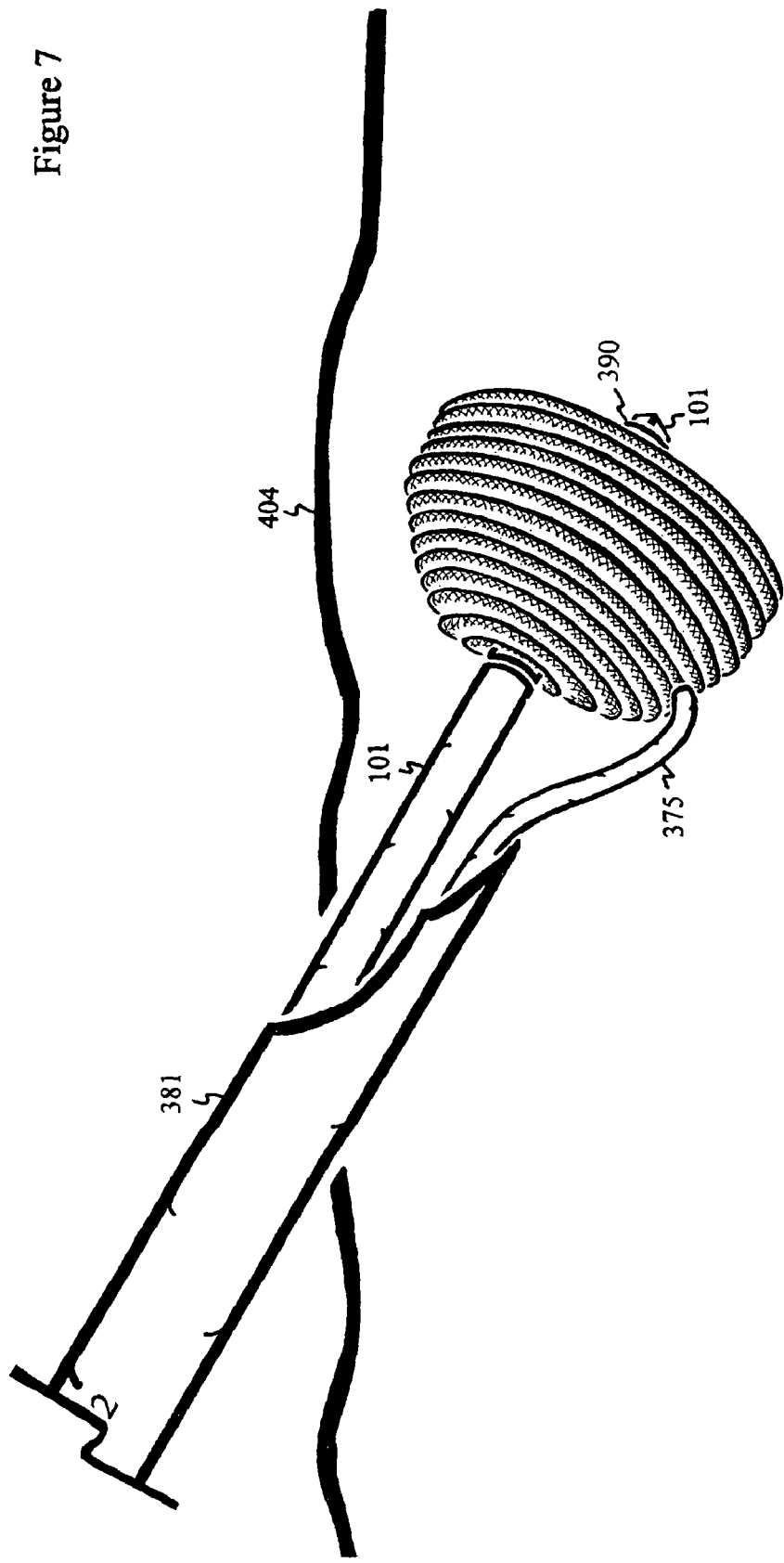
FIG. 7 shows the elastically curved tube 375 guiding the filament 126 to spool over the rotating spindle 390 driven by the blunt rotating needle 101 to bulk or fill the tissue 404.

FIG. 7 shows spooling of the filament 126 guided by the elastically curved tube 375 over the rotating spindle 390 driven by the blunt rotating needle 101 to bulk the tissue 404. The proximal end of the rotating needle 101 contains a handle for cranking. The handle can be connected to gears to facilitate manual operation. Rotation of the rotating needle 101 can also be driven by a motor to expedite spooling.

The lumen separators 430 of the introducer needle 381, as shown in FIG. 2, provide initial support to the elastic tube 375, preventing the elastic tube 375 from pulling into or wrapping around the spool of filament 126. As the spool of filament 126 grows in size, the introducer needle 381 is further withdrawn from the tissue 404 while the blunt needle 101 is held stationary. The elastically curved tube 375 bends outward, staying on top of the growing spool of filament 126, as shown in FIG. 7. The outward bending of the elastically curved tube 375 is supported by the wall of the first lumen 431 of the introducer needle 381 and the surrounding tissue 404.

Figure 8:
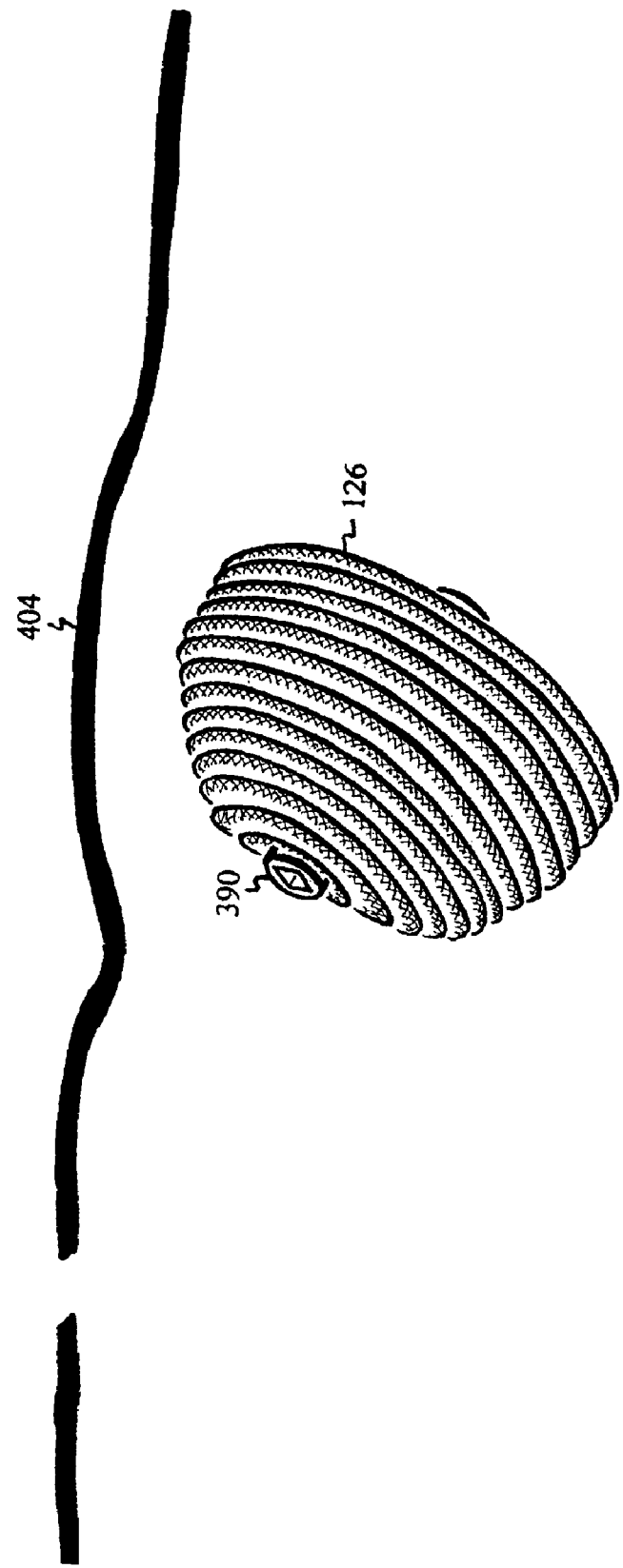
FIG. 8 shows the deployed spindle 390 and spooled filament 126 after withdrawal of the blunt rotating needle 101 and elastically curved tube 375 to bulk beneath the acne scar or tissue 404.

After spooling, the enlarged spool of filament 126 anchored within tissue 404 is much larger than the second lumen 432 of the introducer needle 381. The spooled filament 126 and spindle 390 are deployed, slid or stripped off by holding the introducer needle 381 stationary while withdrawing the rotating needle 101. After withdrawing the elastic tube 375 and introducer needle 381, the pitted tissue or acne scar 404 is bulked, supported or filled by the spool of filament 126 over a biocompatible or degradable spindle 390, as shown in FIG. 8.

In the open position, the L-curve of the elastic tube 375 orients, shifts or guides the advancing filament 126 approximately 90° to the direction of entry to spool over a rotating spindle 390 within tissue 404. The lumen 379 of the elastically curved tube 375 can be polished smoothly by chemical, mechanical or electrical method to minimize friction and tension of the filament 126. Both the lumen 379 and filament 126 can be coated with lubricant. As the spool enlarges within tissue 404, the lubricant also helps to decrease friction between the rotating spool and tissue 404. In addition, lubricant on the filament 126 helps to minimize friction between the rotating spool and the outer surface of the elastic tube 375.

Figure 9:
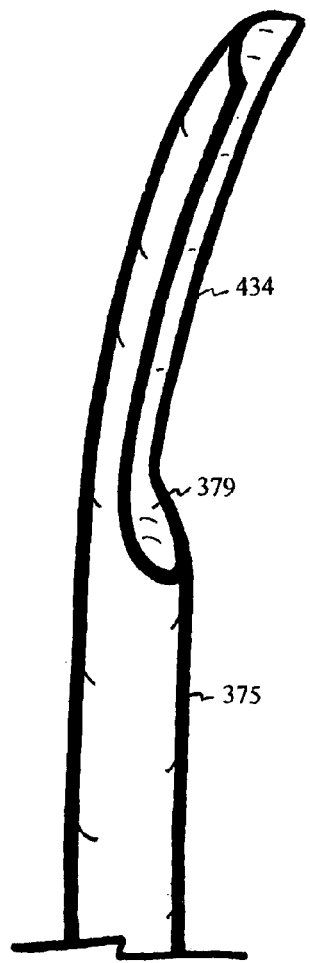
FIG. 9 shows the open distal portion of the elastically curved tube 375 forming an elastic extension arm 434.
Figure 10:
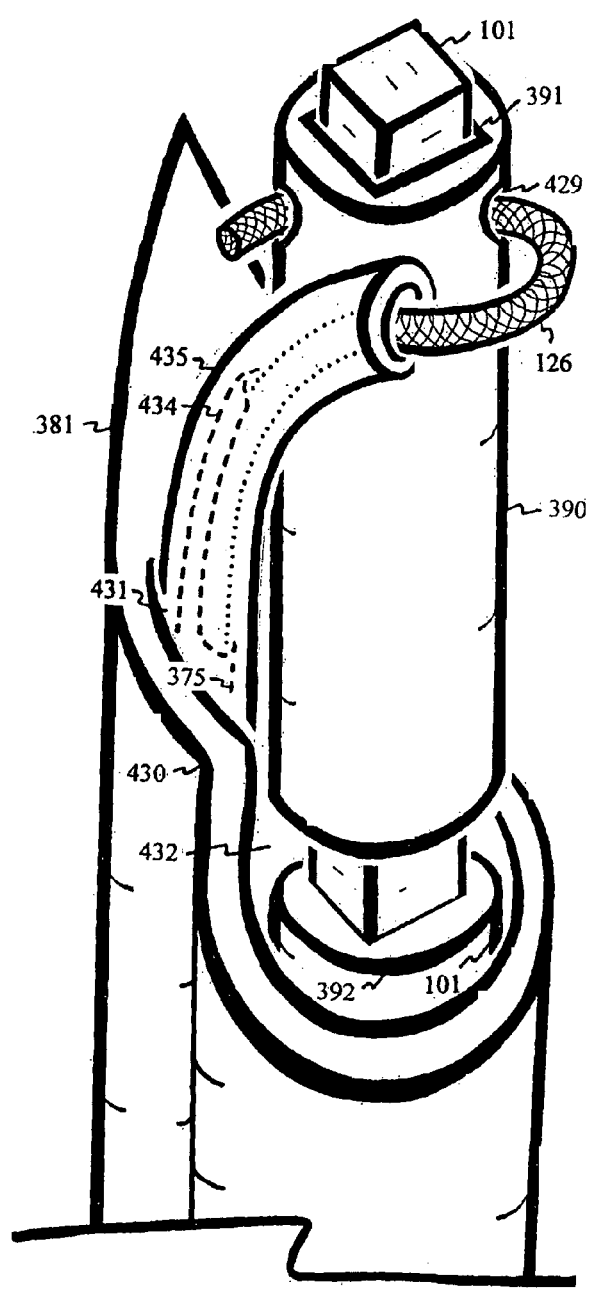
FIG. 10 shows an elastic extension tube 435 inserted over the elastic extension arm 434 providing additional curvature and flexibility to facilitate spooling of filament 126.

A smooth L-curve is also essential to minimize friction between the advancing filament 126 and the lumen 379 of the elastic tube 375. A gradual increment of elasticity helps to smooth the L-curve and avoids kinking, collapsing or snapping the wall of the elastic tube 375. A smooth and increasingly tight curve can also be achieved by using different configurations and/or materials to increase the elastic properties toward the distal end of the elastic tube 375. A distal portion of the elastically curved tube 375 is cut lengthwise forming a curved extension arm 434, as shown in FIG. 9. The concave side of the curvature bends toward the cut side of the extension arm 434. A flexible extension tube 435 is added as a sleeve over the extension arm 434 and elastic tube 375 for additional elasticity, as shown in FIG. 10. The filament 126 from the first lumen 431 is guided by the elastic tube 375, extension arm 434, and extension tube 435 forming a smooth L-curve and attaching to the spindle 390 extended from the second lumen 432 of the introducer needle 381. The filament 126 passes smoothly through the increasingly curved and elastic guiding device orienting from a parallel to a perpendicular position for spooling over the rotating spindle 390.

Figure 11:
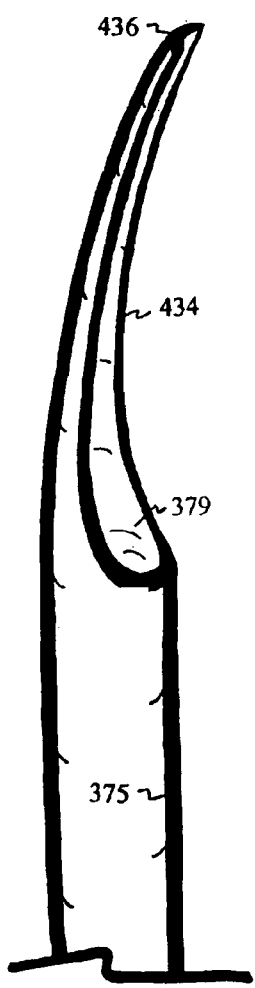
FIG. 11 shows a tapered extension arm 434 with increasing flexibility toward the tapered end 436.
Figure 12:
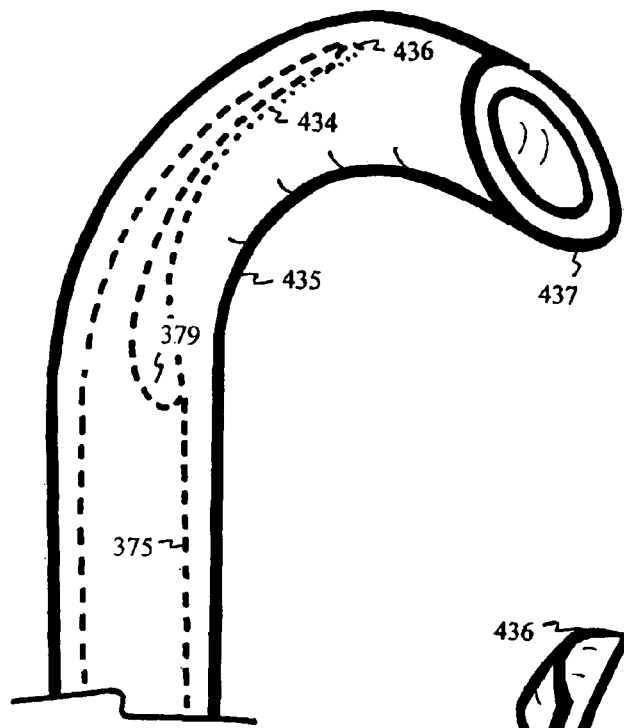
FIG. 12 shows an extension tube 435 over the tapered extension arm 434. The extension tube 435 contains a beveled tip 437 for additional flexibility at the distal end.
Figure 13:
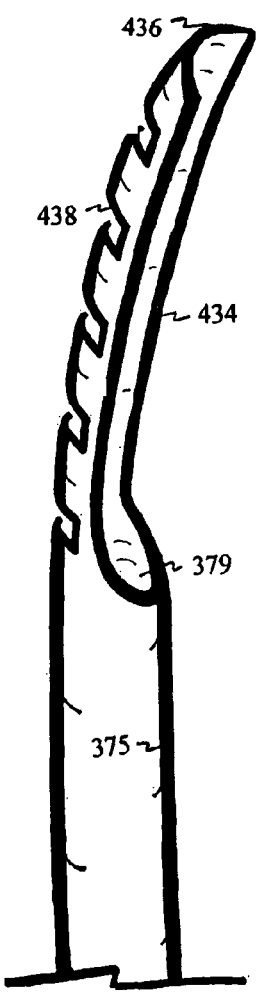
FIG. 13 shows openings or slots 438 on the extension arm 434 for added flexibility.

An increasingly tight curvature of the filament 126 guiding device is made with increasing elasticity toward the distal end. The extension arm 434 can be tapered, beveled, trimmed or thinned toward the distal end 436 to increase elasticity, as shown in FIG. 11. A soft and beveled extension tube 435 can slide over the extension arm 434 to further increase elasticity at the distal beveled tip 437, as shown in FIG. 12. To maximize distal elasticity for a tight and smooth curve, the beveled tip 437 of the extension tube 435 is opposite to the side of the tapered end 436 of the extension arm 434. Slots 438 can also be cut into the extension arm 434 to decrease stress and strain of bending or curving, as shown in FIG. 13. As a result, elasticity of the extension arm 434 increases to accommodate tight and smooth curvatures. The shape, construction and flexibility of the elastic tube 375 can also be similar to a cardiovascular stent.

Figures 14, 15:
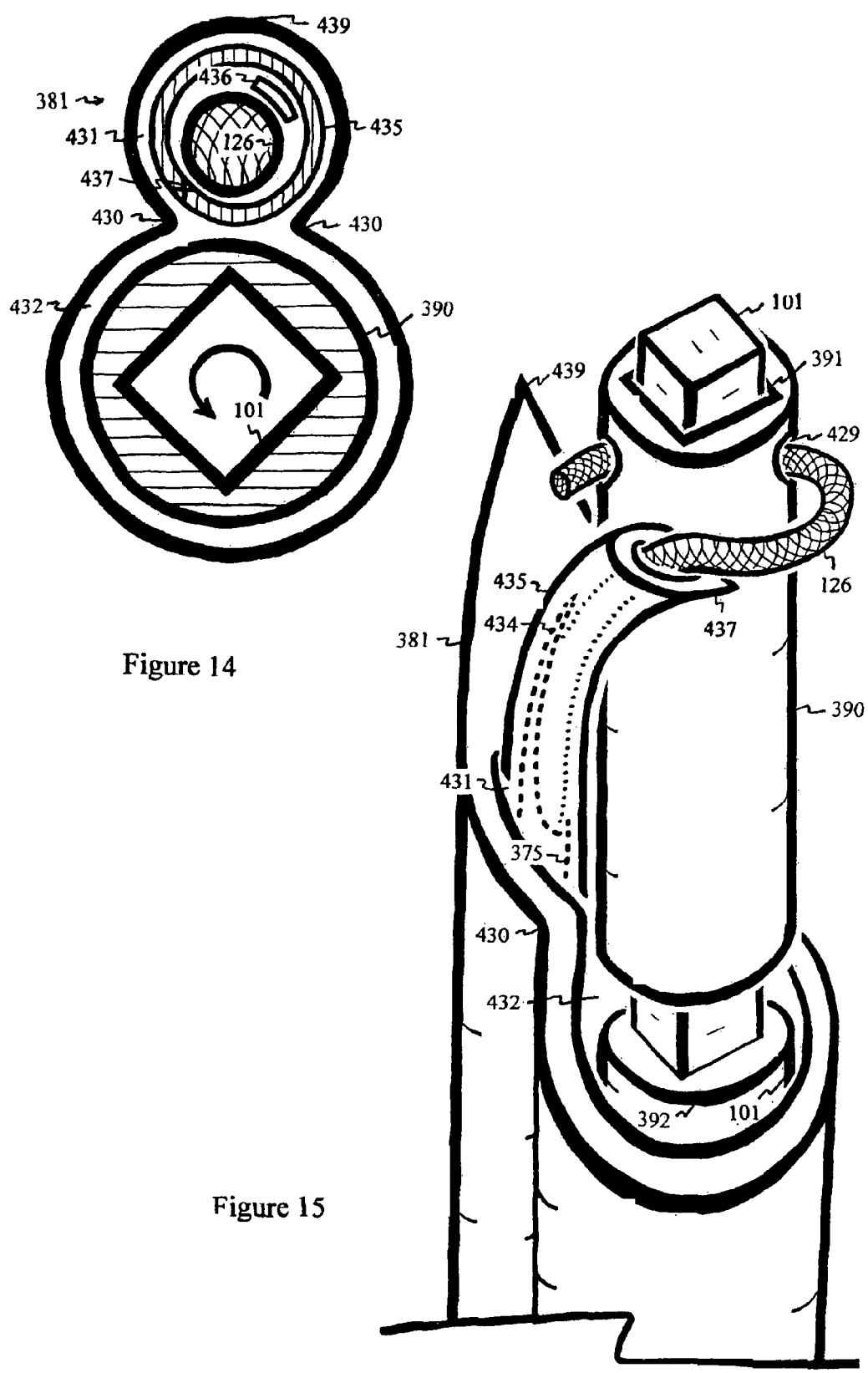
FIG. 14 shows a cross-section of the introducer needle 381 with the filament 126 positioned between the tapered end 436 of extension arm and the beveled tip 437, marked X, of the extension tube 435.
FIG. 15 shows the highly flexible beveled extension tube 435 over the tapered extension arm 434 to guide and facilitate spooling of filament 126 over the spindle 390.

FIG. 14 shows a cross-section of the introducer needle 381 with extension tube 435, tapered end 436 of extension arm 434 and filament 126 in the first lumen 431, and the rotating needle 101 within the spindle 390 in the second lumen 432. For a tight and smooth curve, the beveled tip 437, marked X in FIG. 14, of the extension tube 435 is opposite to the side of the tapered end 436 of the extension arm 434. The filament 126 is guided through the curvature of the tapered extension arm 434 into the flexible extension tube 435. The filament 126 is further guided within an even more elastic beveled tip 437 of the extension tube 435 into a tighter curve to align the filament 126 and spool over the rotating spindle 390 driven by the rotating needle 101. FIG. 15 shows a tight and smooth curve by combining the tapered extension arm 434 and beveled extension tube 435 to guide the filament 126 from a parallel entry position to the perpendicular spooling position, spooling over the rotating spindle 390. Both elasticity and curvatures progressively increase from the shaft of elastic tube 375, tapered extension arm 434 and extension tube 435 to the beveled tip 437 of the extension tube 435, forming tight and smooth curvatures to orient the filament 126 for spooling. The tight curvatures may have multiple radii decreasing with progression toward the distal tip 437 of the elastic extension tube 435. The tapered extension arm 434 serves as a curved and flexible anchoring post, supported by the lumen separator 430, as shown in FIG. 15, to prevent the flexible extension tube 435 from winding around the spindle 390 during spooling.

The sharp and beveled tip 439 of the introducer needle 381 is preferred near the first lumen 431 to function as a lengthened support to the elastic tube 375, as shown in FIG. 15. In addition, tissue puncture of the introducer needle 381 is gradual from the thin portion containing the first lumen 431 to the thick portion containing the second lumen 432.

Modifications can be made with the spooling device. The rotating needle 101 can be sharpened with tissue puncturing capability, as shown in FIG. 16. The spindle 390 can have proximal and distal tapered edges 398, as shown in FIG. 17, to maintain and guide spooling of the filament 126 within the spindle 390. The connection between the rotating needle 101 and spindle 390 can be a tongue and grove arrangement. A protrusion 393 from the rotating needle 101 is sized and configured to fit into an indentation 394 of the spindle 390 for rotation and deployment, as shown in FIG. 18.

The elastically curved tube 375 can be latched or connected to the rotating needle 101 for tissue puncturing. A window 402 and a groove 405 are open to the distal end of the elastically curved tube 375. The elastically curved tube 375 with the window 402 and the groove 405 can be resiliently straightened, as shown in FIG. 19. The β angle of the distal end 401 of the elastic tube 375 and the γ angle of the proximal wall 380 of the window 402 in FIG. 19 are acute angles to facilitate tissue 404 puncturing. The θ angle of the distal wall 400 of the window 402 is also an acute angle to facilitate withdrawal of the elastic tube 375 after completion of spooling.

The distal end with the groove 405 of the elastic tube 375 slides over and grips the rotating needle 101, as shown in FIG. 20, to fasten and support the distal end of the elastic tube 375 for tissue 404 puncturing. The distal end of the spindle 390 in FIG. 20 is tapered to facilitate tissue 404 puncturing. As the size of spooled filament 126 increases over the spindle 390, the rotating spool pushes outwardly against the window 402 of the elastic tube 375 to dislodge or push out the distal end of the elastic tube 375 from the rotating needle 101 through the groove 405. The elastic tube 375 moves from the closed position to open position within tissue 404. The dislodged distal end of the elastic tube 375 extends and protrudes outwardly to be embedded, anchored or supported by surrounding tissue 404 to allow additional spooling of filament 126.

Stacking the elastically curved tube or filament guide 375 over the rotating needle 101 can help tissue 404 puncture. FIG. 21 shows an elastically curved tube 375 being resiliently straightened. The resiliently straightened tube 375 has a window or opening 402 with similar angles as FIG. 19. The .beta. angle at the distal end 401 of the elastic tube 375 and the .gamma. angle of the proximal wall 380 of the window 402 in FIG. 21 are acute angles to facilitate tissue 404 puncturing. The .theta. angle of the distal wall 400 of the window 402 is also an acute angle to facilitate withdrawal of the elastic tube 375 after completion of spooling. A rotating needle 101 is inserted into the lumen 379 of the resiliently straightened tube 375, forming a first or closed position of the elastically curved tube 375, as shown in FIG. 22. A filament 126 is inserted into the lumen 269 of the rotating needle 101 prior to tissue 404 puncturing.

Figure 23:
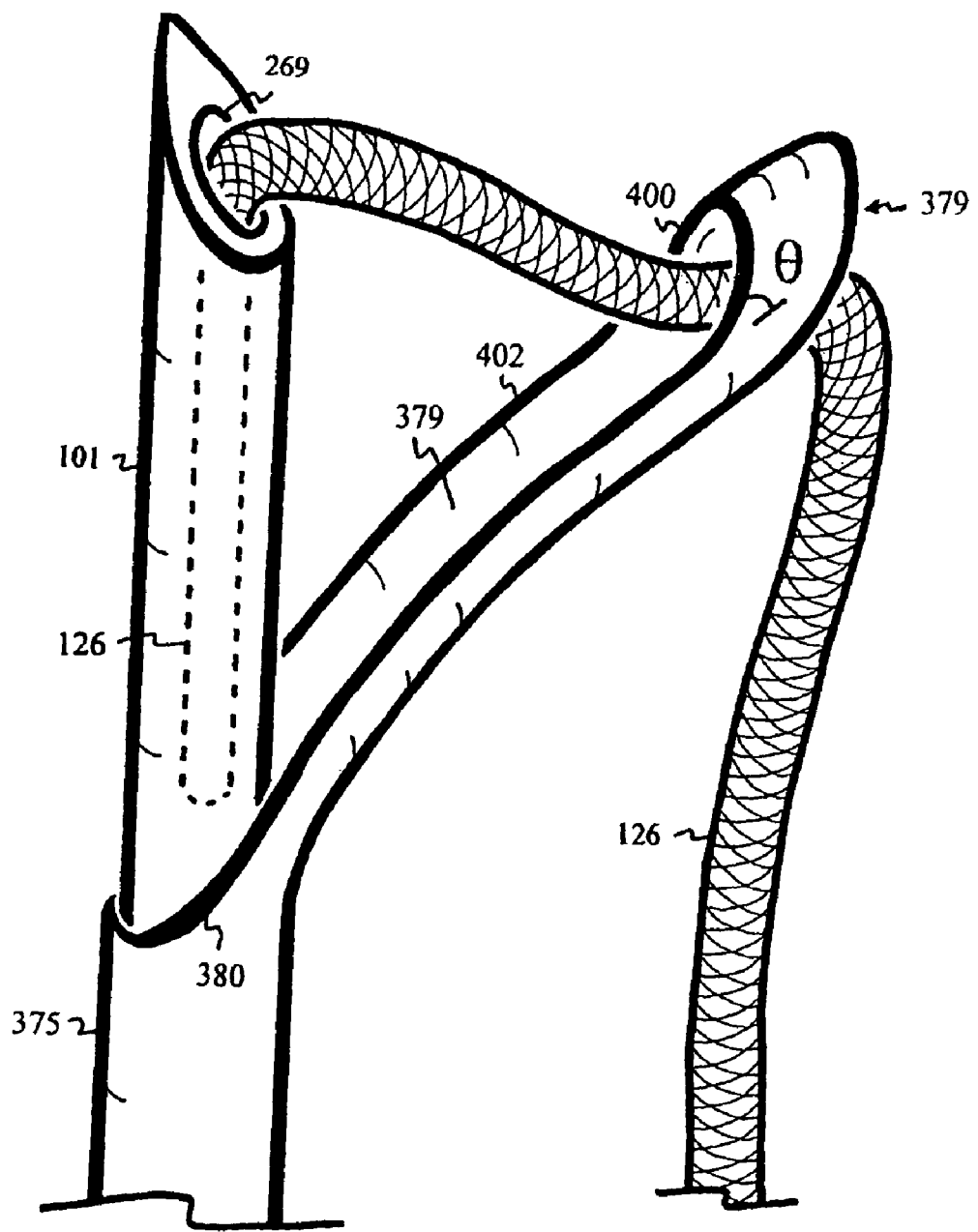
FIG. 23 shows rotating needle 101 withdrawn from the distal portion of the elastic tube 375 to allow resumption of curvature of the elastic tube 375, thus directing filament 126 spooling over the rotating needle 101.
Figure 24:
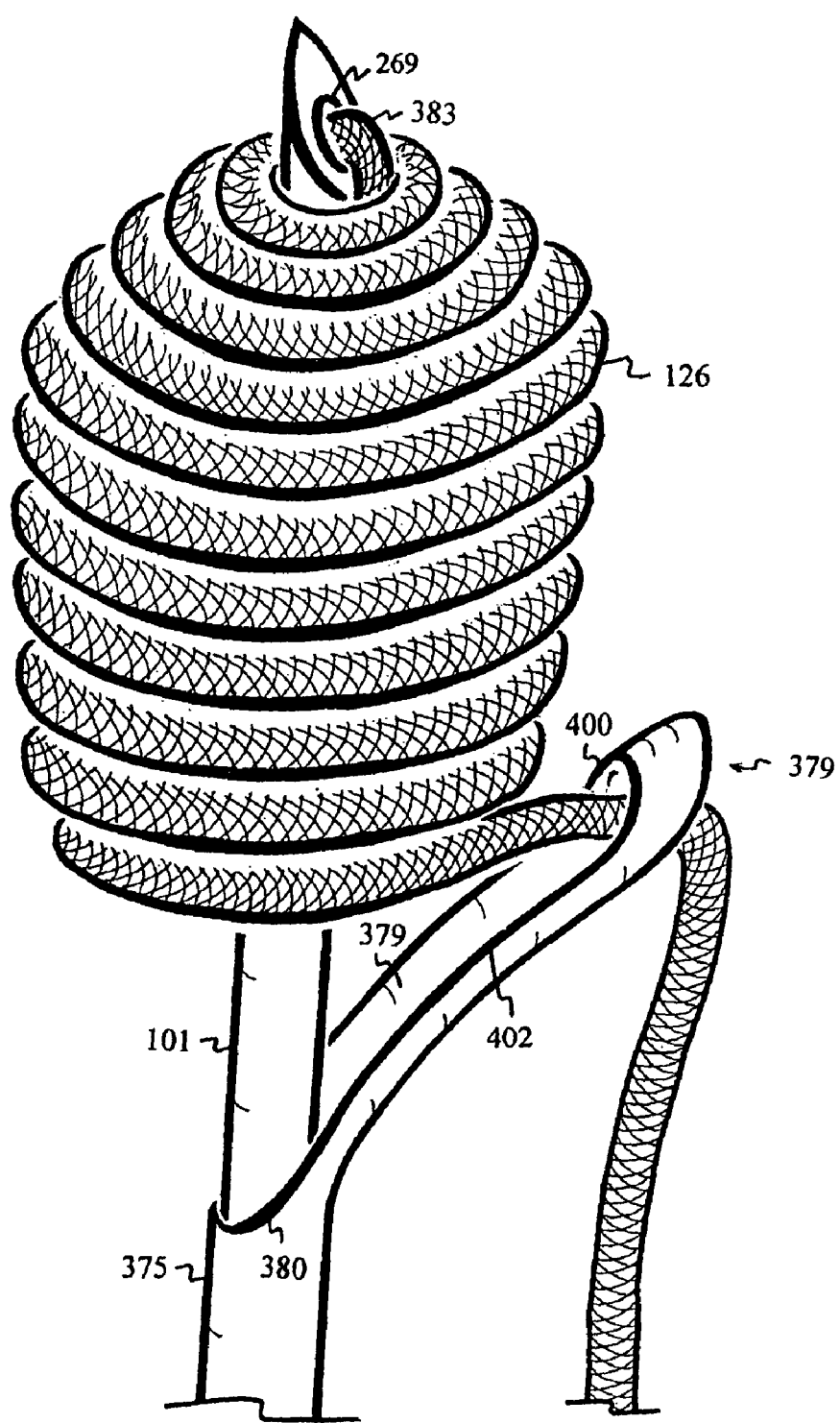
FIG. 24 shows spooling of the filament 126 over the beveled end of the rotating needle 101.

After tissue 404 puncturing, the elastically curved tube 375 is deployed into an open or second position by withdrawing the rotating needle 101 from the distal portion of the elastically curved tube 375, as shown in FIG. 23. The distal portion of the elastically curved tube 375 resumes the resilient curvature, allowing the rotating needle 101 to protrude through the window 402. The distal portion of the elastically curved tube 375 separates from the rotating needle 101. The distal portion of the elastically curved tube 375 still engages, holds and guides spooling of the filament 126 away or generally perpendicularly to the rotating needle 101. As the rotating needle 101 rotates, the beveled tip of the rotating needle 101 catches, winds and spools the filament 126 over the shaft of the rotating needle 101, as shown in FIG. 24. The portion 383 of the filament extends into and freely spins within the lumen 269 of the rotating needle 101 during spooling. The spool of filament 126 is lengthened by a gradual withdrawal of the elastically curved tube 375, as shown in FIG. 24. Upon completion of spooling, the elastically curved tube 375 is withdrawn from tissue 404. The acute angle .theta., as shown in FIGS. 21 and 23, of the distal wall 400 of the window 402 accommodates withdrawal of the elastically curved tube 375.

As the spool of filament 126 enlarges, it anchors and fastens within the tissue 404. The spooled filament 126 is deployed, slid or stripped off the shaft of the rotating needle 101 by holding the elastic tube 375 while withdrawing the rotating needle 101. The portion of filament 383 within the lumen 269 of the rotating needle 101 freely slides out to deploy the spool of filament 126 and bulk or fill the tissue 404.

The elastically curved tube 375 and rotating needle 101 can have a lubricant coating to minimize friction for filament 126 passage and spool deployment. The lubricant can be acrylic, AlTiN, ceramic, chrome, CrN, cross linked polyethylene glycol, diamond-like DIAMONEX®, DICRONITE®, ECO-BRITE™, ECO-LAST™, epoxy, fluorinated ethylene propylene, fused silica, hyaluronan, HYDAK®, hydrogel, HYDROMER®, HYDRO-SIL™, KRYTOX®/VYDAX®, low friction chromium, LUBRICOAT®, LUBRILAST™, ME-92®, MEDCOAT 2000™, MEDI-COAT®, MELONITE®, MOLECULAR-PTFE™, molybdenum disulfide, $MoS_2Ti$, $MoS_2Ti$-SIP, Ni—Ag/$MoS_2$, NiCoTef®, $NiR_c63$ nickel, NITUFF®, Nylon, PARYLAST™, PARYLENE®, PD-SLICK™, PHOTOLINK®, plasma, polyamide, polyethylene glycol, polyurethane, poly-xylene, PTFE, $R_c$65-68, silicone, SILVERSTONE®, SLIP-COAT®, STAY-WET™, SUPER-SLIP™, TEFLON FEP®, TEFLON PFA®, TEFLON TFE®, TEFLON-S®, TEFZEL/ETFE®, TiAlN, TiCN, titanium nitride, ultra high molecular weight polyethylene, VICOAT™, XYLAN® or ZrN. The method for coating the elastically curved tube 375 or rotating needle 101 can be anodizing, chemical crosslinking, cryo treating, dipping, electro-chemical polishing, electrolyzing, ion implanting, photo activating, plasma, plating, spraying, UV-curing, vacuum depositing or vapor depositing.

The rotating needle 101 or elastically curved tube 375 can be coated with radiopaque, echogenic, MRI visible coating or other coatings to assist guidance and enhance imaging.

The filament 126 can be coated with a lubricant, swellable material and/or image enhancing material. The lubricant can be silicone, fatty acid, lecithin, polyurethane or other. The lubricant can also be activated by moisture to form a hydrogel. The hydrogel can expand or swell to further increase the size or the bulk of the spool of filament 126. The expanding or swelling agent can be polyethylene glycol, cross-linked polyethylene glycol, collagen, alginate, hyaluronate, elastin or other. A radiopaque, echogenic, MRI visible coating on the filament can help clinician to locate or observe the spool of filament 126. The filament 126 can also be coated with radioactive elements, such as iodine 125, for cancer or other therapeutic treatment.

Figure 25:
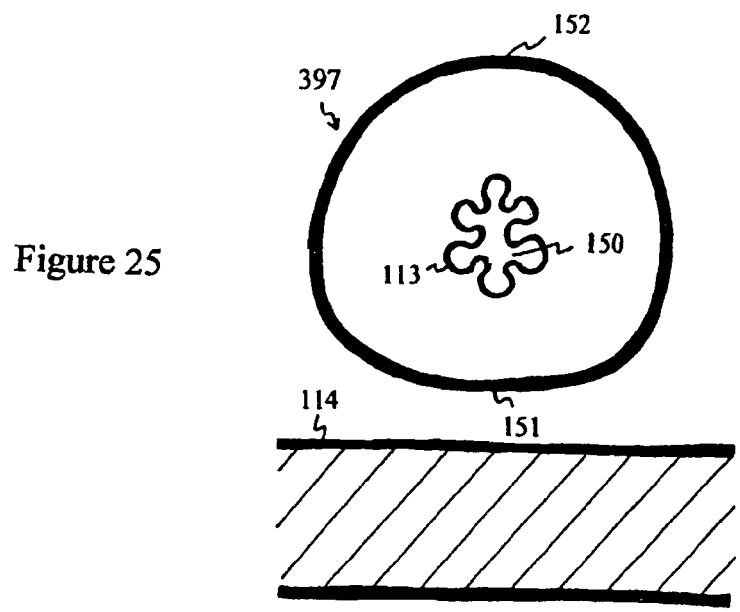
FIG. 25 shows a cross-section of urethra 397 with open urethral lumen 150 unsupported by the anterior vaginal wall 114.
Figure 26:
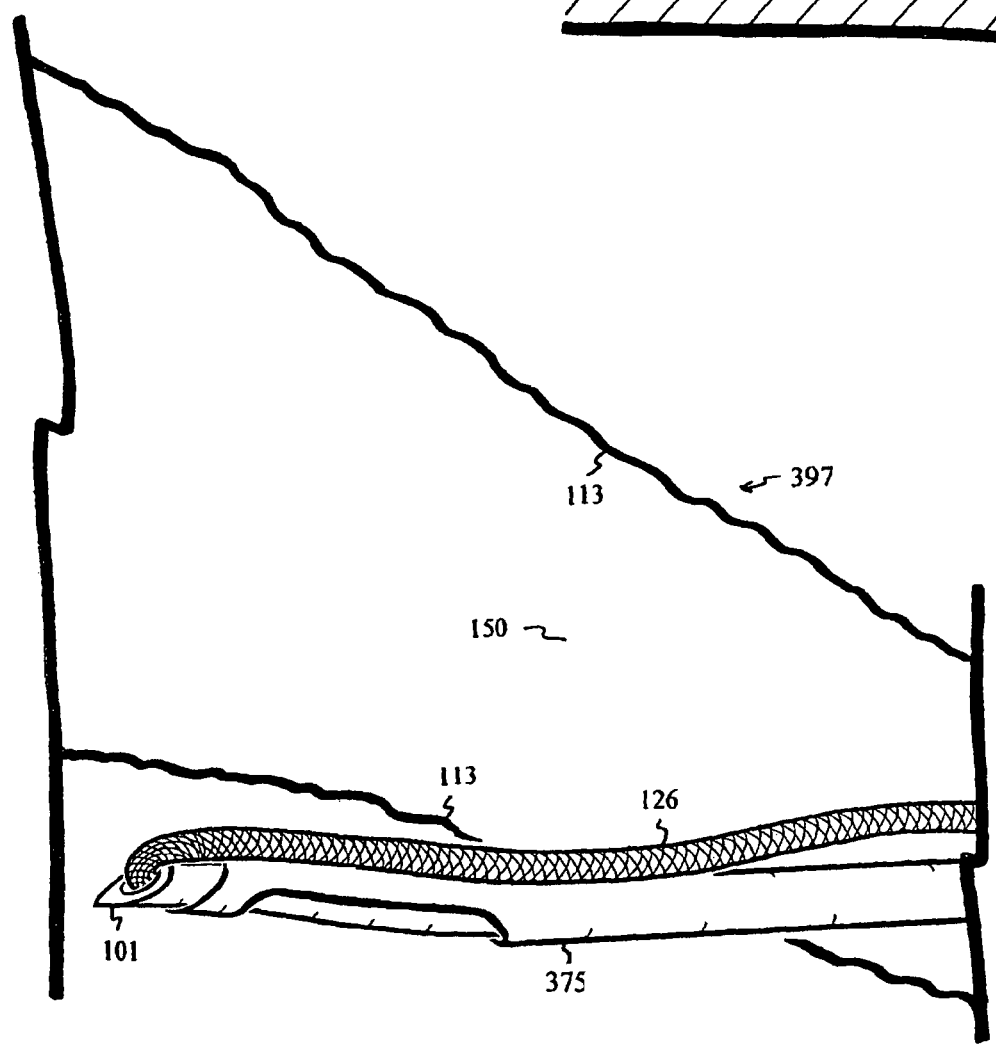
FIG. 26 shows mucosal 113 puncture by the rotating needle 101 delivering the elastically straightened tube 375 and filament 126 through the urethral lumen 150.
Figure 27:
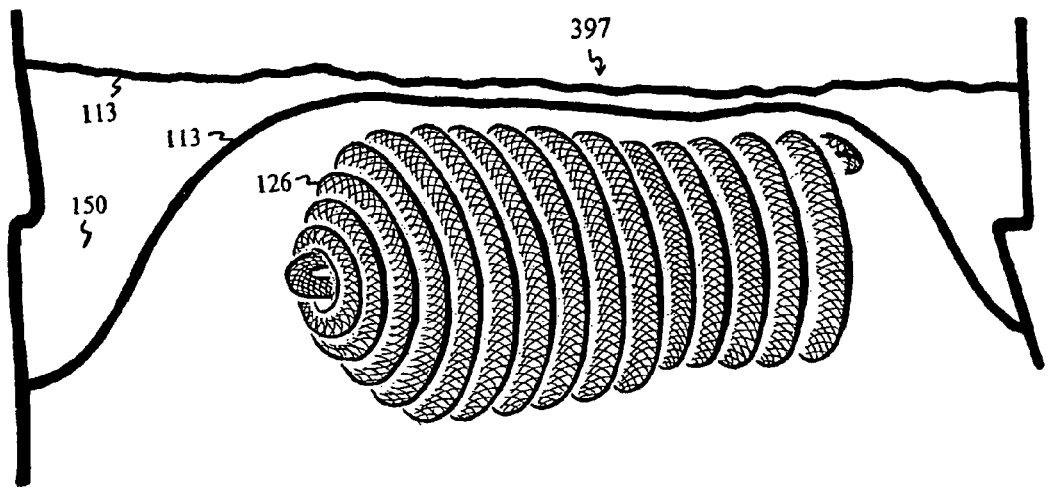
FIG. 27 shows a spool of filament 126 bulking the mucosa 113 to narrow or close the urethral lumen 150 to treat urinary stress incontinence.
Figure 28:
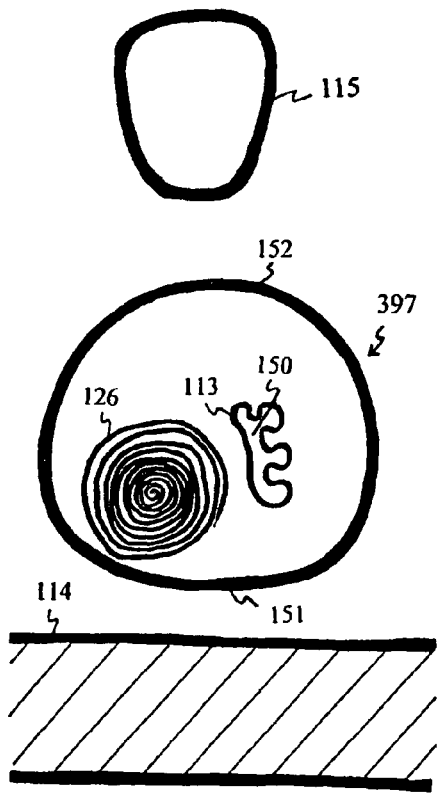
FIG. 28 shows a cross-sectional view of partial lumen 150 closure by using the spool of filament 126 to bulk up the mucosa 113.
Figure 29:
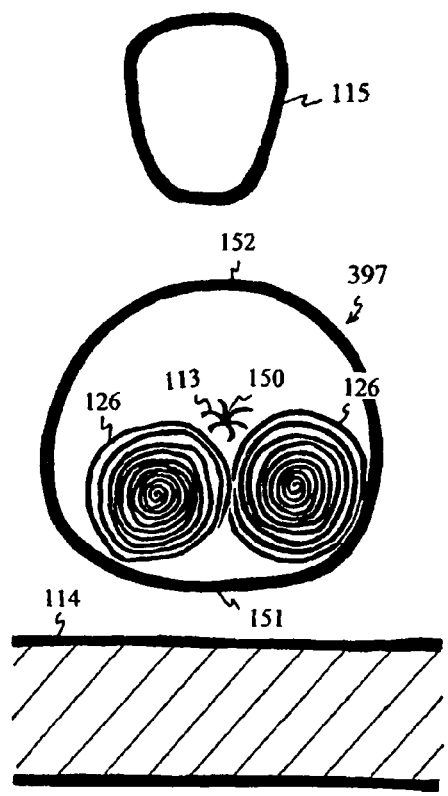
FIG. 29 shows closure of urethral lumen 150 using two spools of filament 126 to bulk up the mucosa 113 to treat urinary stress incontinence.

FIG. 25 shows a cross-section of urethra 397 with an open urethral lumen 150 unsupported by the anterior vaginal wall 114, a factor causing urinary stress incontinence. In FIG. 26, the elastically curved tube 375 is resiliently straightened over the rotating needle 101, carries the filament 126 through the lumen 150 of the urethra 397 and punctures the mucosa 113, preferably near the bladder neck. The rotating needle 101, elastically curved tube 375 and filament 126 can be covered by a thin, retrievable and blunt tube or sleeve for insertion into the urethral lumen 150. The rotating needle 101 will then extend from the blunt tube to puncture the mucosa 113. The filament 126 is completely spooled into the mucosa 113 by the method described in FIGS. 22 to 24. Both the rotating needle 101 then elastically curved tube 375 are withdrawn to deploy the spooled filament 116 in mucosa 113, as shown in FIG. 27. The mucosa 113 is bulked, raised, lifted, supported or enlarged by the spooled filament 126 to narrow or close the lumen 150 of the urethra 397, as shown in FIG. 28. Collagen is commonly used to bulk and treat urinary stress incontinence. The preferred mucosal injections of collagen are around the posterior bladder neck and in front of the anterior vaginal wall 114. FIG. 28 shows a cross-section of the urethra 397 with the spool of filament 126 implanted near the 8 o'clock position, relative to the pubis 115 at the 12 o'clock position. FIG. 29 shows a cross-section of the urethra 397 bulked by two spools of filaments 126 near the 4 o'clock and 8 o'clock positions to occlude the lumen 150 and minimize stress urinary incontinence.

The spindle 390 and the blunt rotating needle 101 of FIG. 15 can be substituted with the beveled rotating needle 101 with a lumen 269. The lumen 269 is used to anchor the filament 126 from the filament guiding device, which may include the elastic tube 375, elastic extension arm 434, extension tube 435 and beveled tip of extension tube 437. The beveled distal end of the rotating needle 101 is used to wind or spool the filament 126 over the shaft of the rotating needle 101, similar to the spooling process in FIG. 24. The spooled filament 126 within tissue becomes significantly wider than the diameter of the second lumen 432 of the introducer needle 381 of FIG. 15. The spooled filament 126 can be deployed by holding the introducer needle 381 stationary while withdrawing the rotating needle 101 to strip or slide the spooled filament 126 off the shaft of the rotating needle 101. Sequential withdrawal of the rotating needle 101, the filament guiding device and the introducer needle 381 is used to deploy the spooled filament 126 for bulking and repairing tissue.

Figures 30, 31:
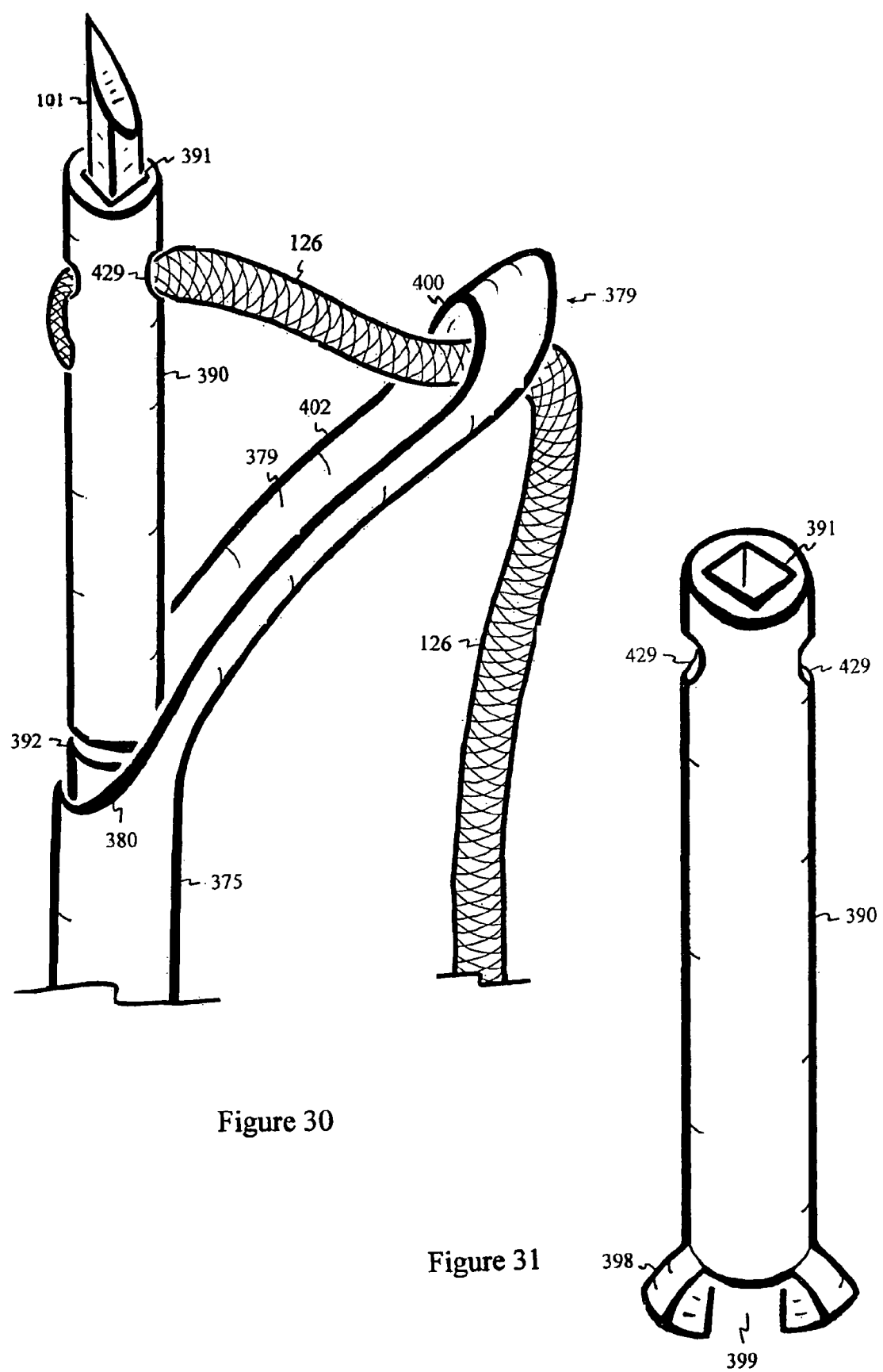
FIG. 30 shows the spindle 390, rotating needle 101 and elastically curved tube 375 with the window 402 in an open position for spooling filament 126.
FIG. 31 shows an indentation 399 on the tapered edge 398 of the spindle 390 to accommodate the closed position of the elastically curved tube 375.

For ease of deploying the spooled filament 126 within tissue, the rotating needle 101 with the spindle 390 can be inserted into the lumen 379 of the elastically curved tube 375, as shown in FIG. 30. The spindle 390 can also have a tapered edge 398 to guide spooling of the filament 126. FIG. 31 shows an indentation 399 in the tapered edge 398 to accommodate the closed position of the elastically curved tube 375.

Figure 32:
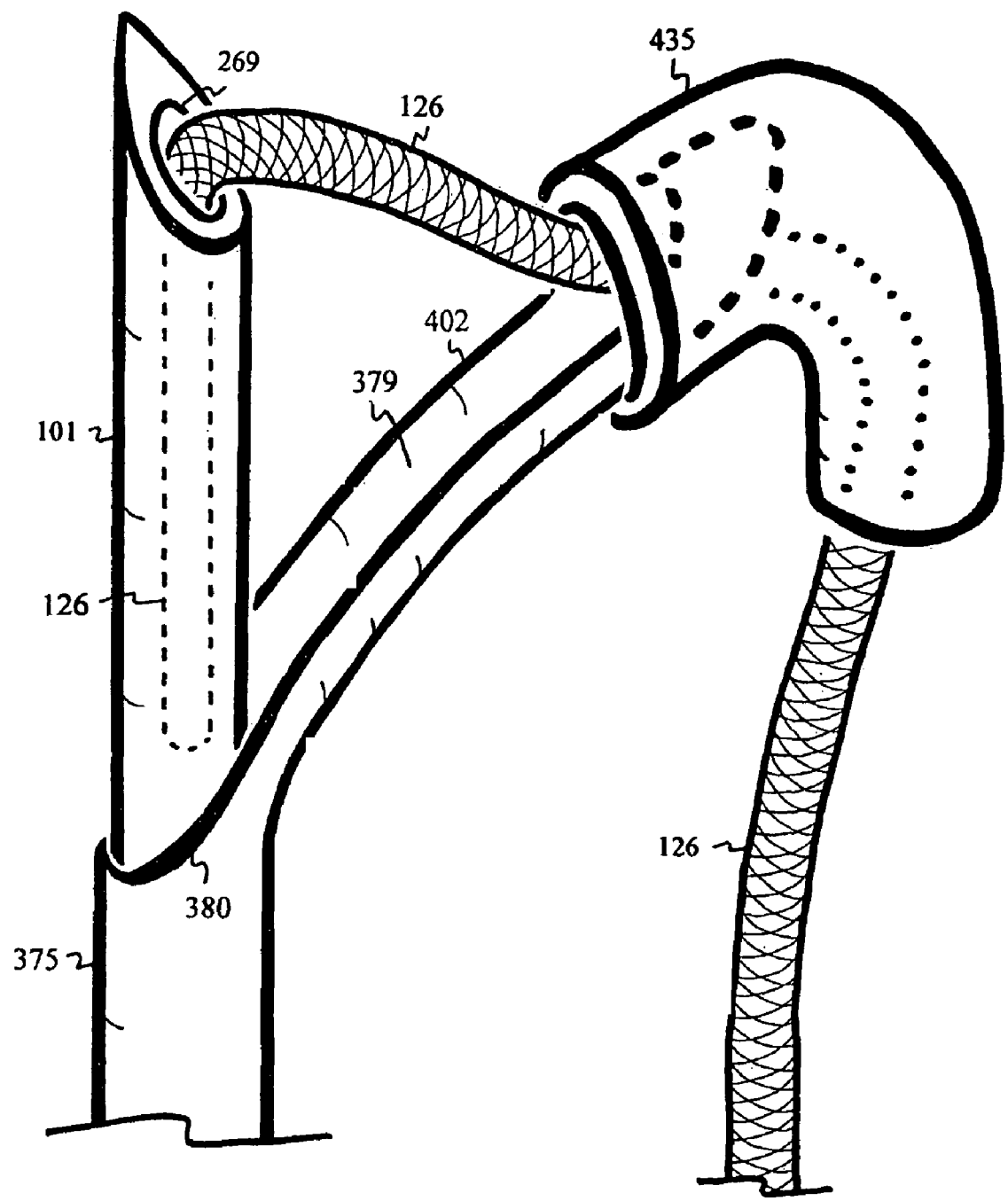
FIG. 32 shows an extension tube 435 inserted over the distal end of the elastically curved tube 375 to facilitate passage of the filament 126.

A flexible extension tube 435 can facilitate smooth passage of the filament 126 through the distal end of the elastically curved tube 375, as shown in FIG. 32, to spool over the rotating needle 101.

Figures 33, 34:
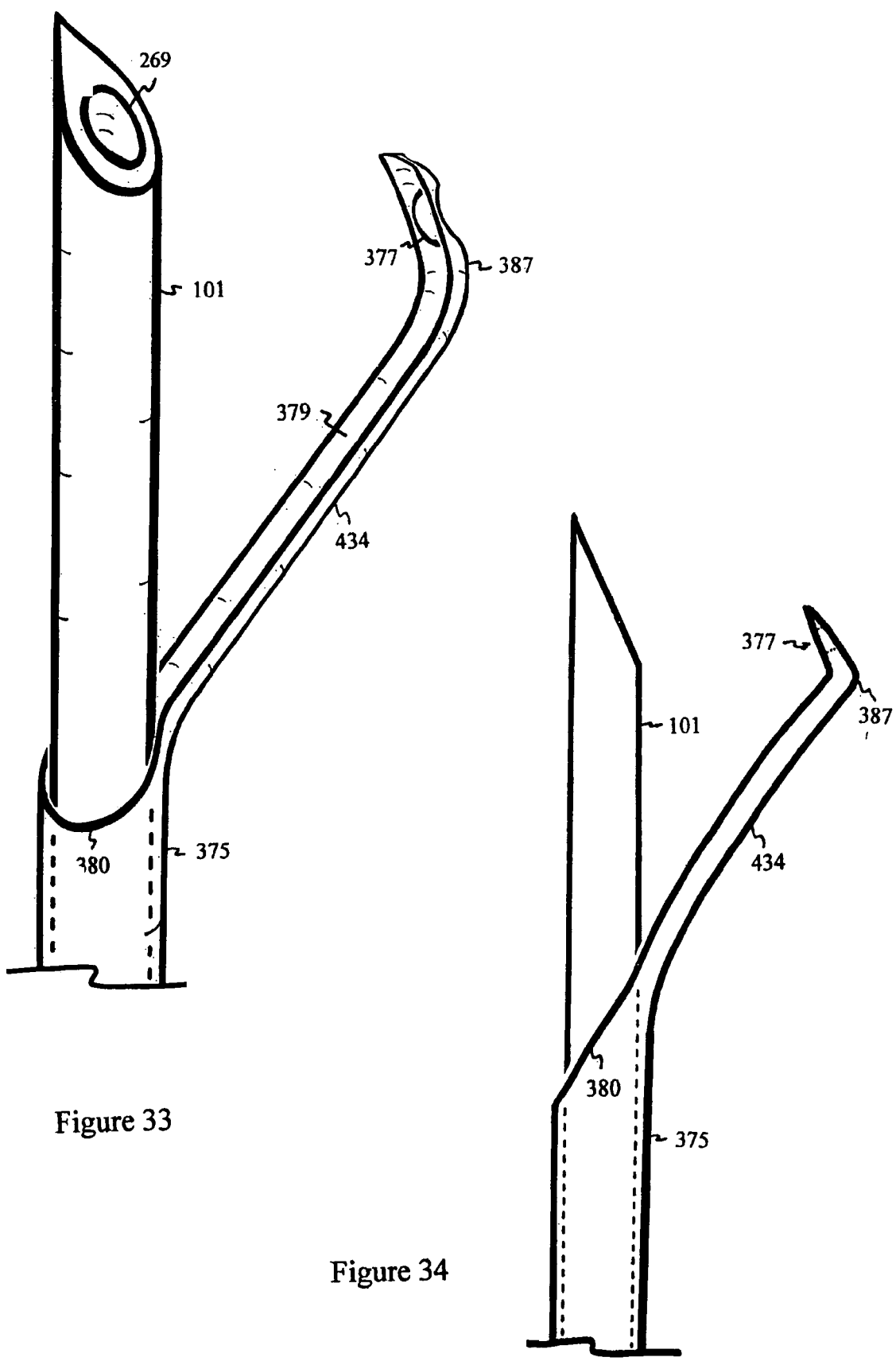
FIG. 33 shows a hole 377 and a bend 387 on an extension arm 434 formed at the distal portion of the elastically curved tube 375.
FIG. 34 shows a side view of the extension arm 434 in an open position, away from the rotating needle 101.
Figure 35:
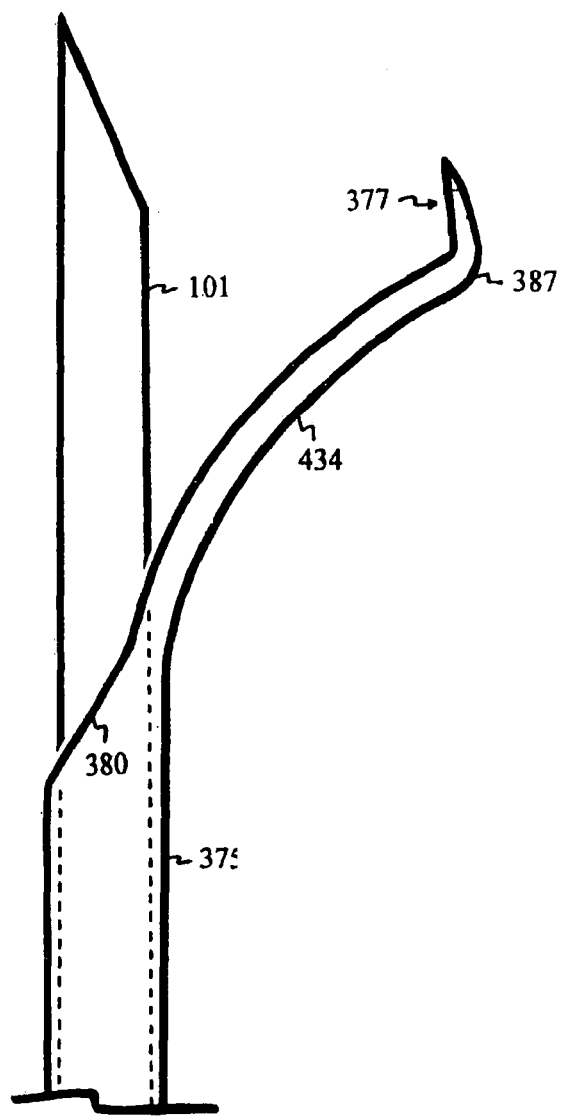
FIG. 35 shows the extension arm 434 further curved away from the rotating needle 101.
Figure 36:
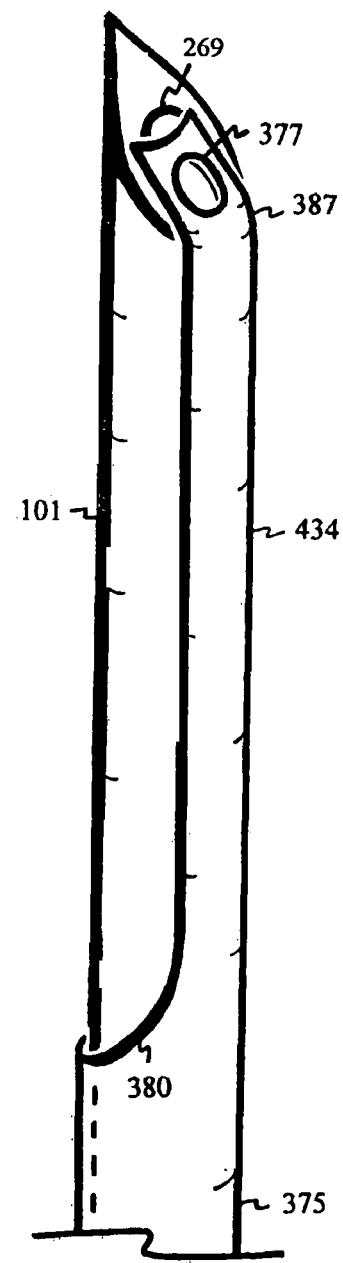
FIG. 36 shows the closed position of the extension arm 434 adjacent to the rotating needle 101.

Similar to the window 402 in FIG. 21, an elastic extension arm 434 can be formed at the distal portion of the elastically curved tube 375, as shown in FIG. 33 in an open position. The elastic extension arm 434 contains a hole 377 and a bend 387 near the distal end. The rotating needle 101 is partially housed within the lumen 379 of the elastic tube 375. The lumen 379 of the elastic tube 375 becomes a trough 379 of the elastic extension arm 434. FIG. 34 shows a side view of the rotating needle 101 and elastic extension arm 434. The body of the elastic extension arm 434 can also be curved to widen the open position, as shown in FIG. 35. In a closed position, the elastic extension arm 434 resiliently approximates the rotating needle 101, as shown in FIG. 36. The bend 387 of the elastic extension arm 434 aligns the hole 377 of the elastic extension arm 434 over the lumen 269 of the rotating needle 101.

Both the window 402 and elastic extension arm 434 of the elastic tube 375 can be created by laser, electric discharge, water jet, machining or other technique. The proximal walls 380 of the window 402 and extension arm 434 in FIGS. 21 and 33 are beveled to facilitate tissue puncturing.

Figure 39:
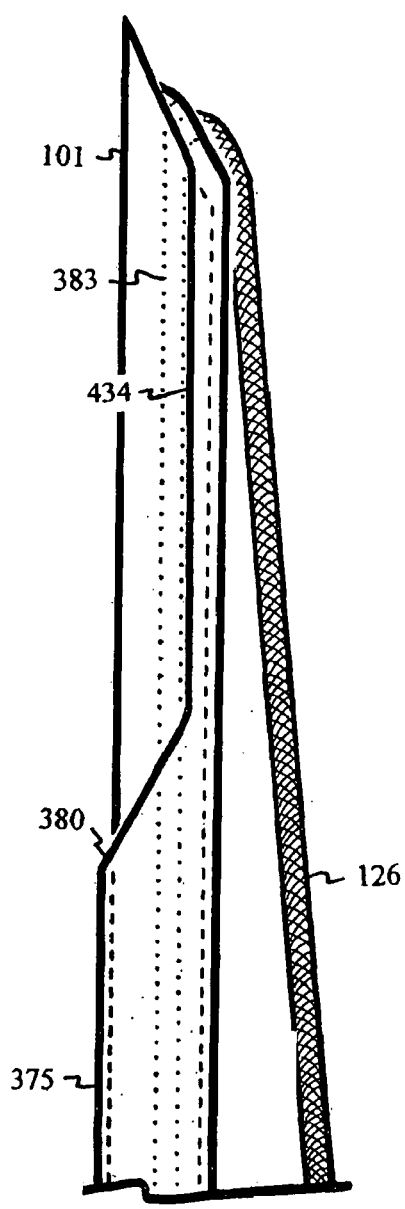
FIG. 39 shows a side view of the rotating needle 101 and filament 126 under tension to keep the elastically curved extension arm 434 in the closed position.
Figure 40:
FIG. 40 shows the closed position of the elastically curved extension arm 434 within the lumen 382 of an introducer needle 381.

FIG. 37 shows a filament 126 threaded through the hole 377 of the elastic extension arm 434 into the lumen 269 of the rotating needle 101. The elastic tube 375 directs the spooling process of the filament 126 by sliding over the rotating needle 101. With the portion of filament 383 anchored within the lumen 269 of the rotating needle 101, the tension and position on the filament 126 may be adequate to maintain the closed position of the elastic extension arm 434, as shown in FIG. 38, a side view in FIG. 39. The closed position of the elastic extension arm 434 can also be maintained within the lumen 382 of the introducer needle 381, as shown in FIG. 40. The filament 126 extending from the lumen 269 of the rotating needle 101 and the hole 377 of the elastic extension arm 434 can be draped outside or within the lumen 382 of the introducer needle 381. The introducer needle 381 has tissue-puncturing capability to deliver the rotating needle 101, elastic extension arm 434 and filament 126 into tissue. The introducer needle 381 is then partially withdrawn while holding and exposing the rotating needle 101 and elastic extension arm 434 within tissue. The elastic extension arm 434 resumes the resilient curvature moving from the closed to open position within tissue, similar to FIG. 37, to position the filament 126 for spooling.

Figure 41:
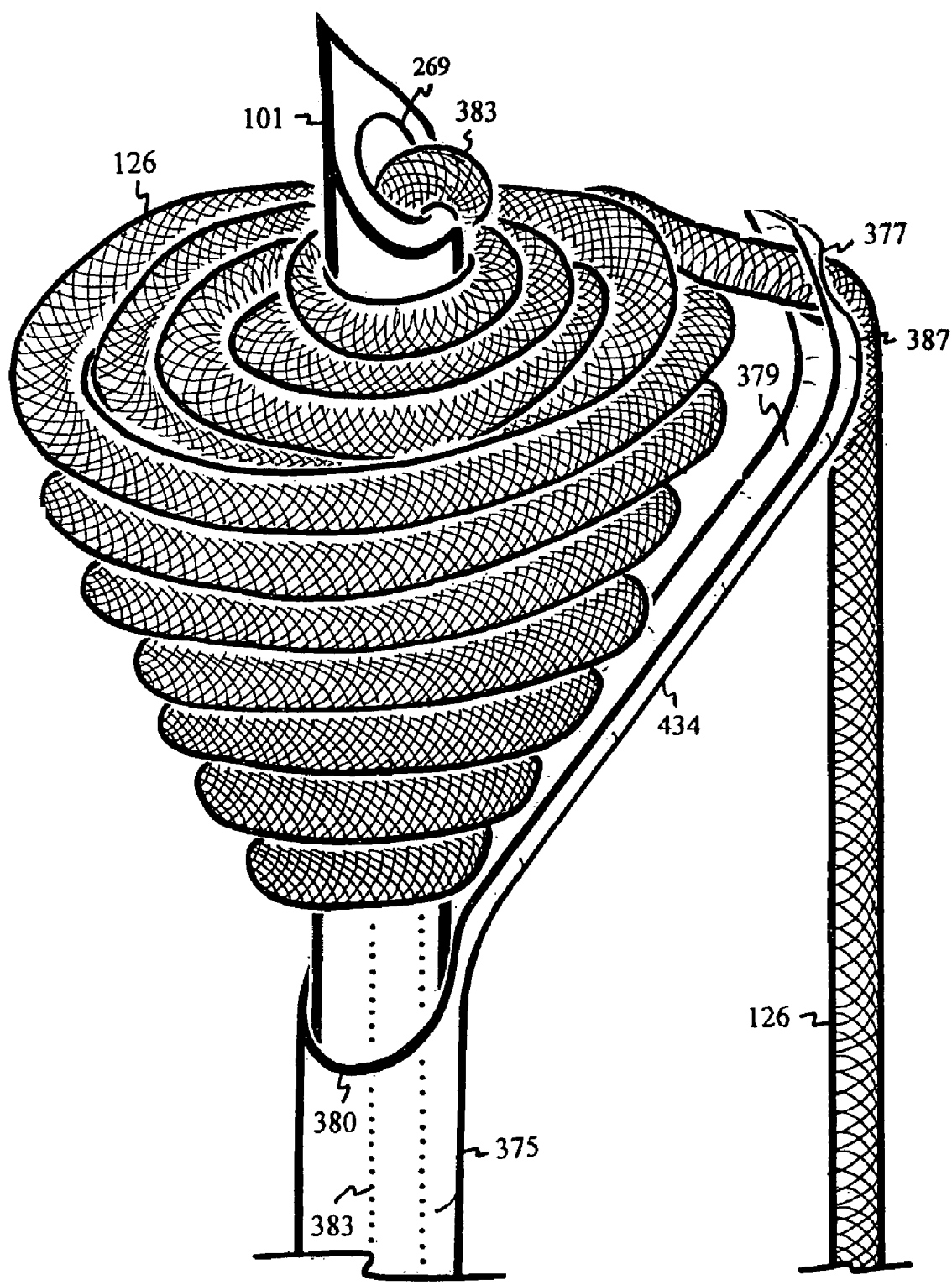
FIG. 41 shows spooling of the filament 126, guided through the hole 377 of the open extension arm 434 over the rotating needle 101.
Figure 42:
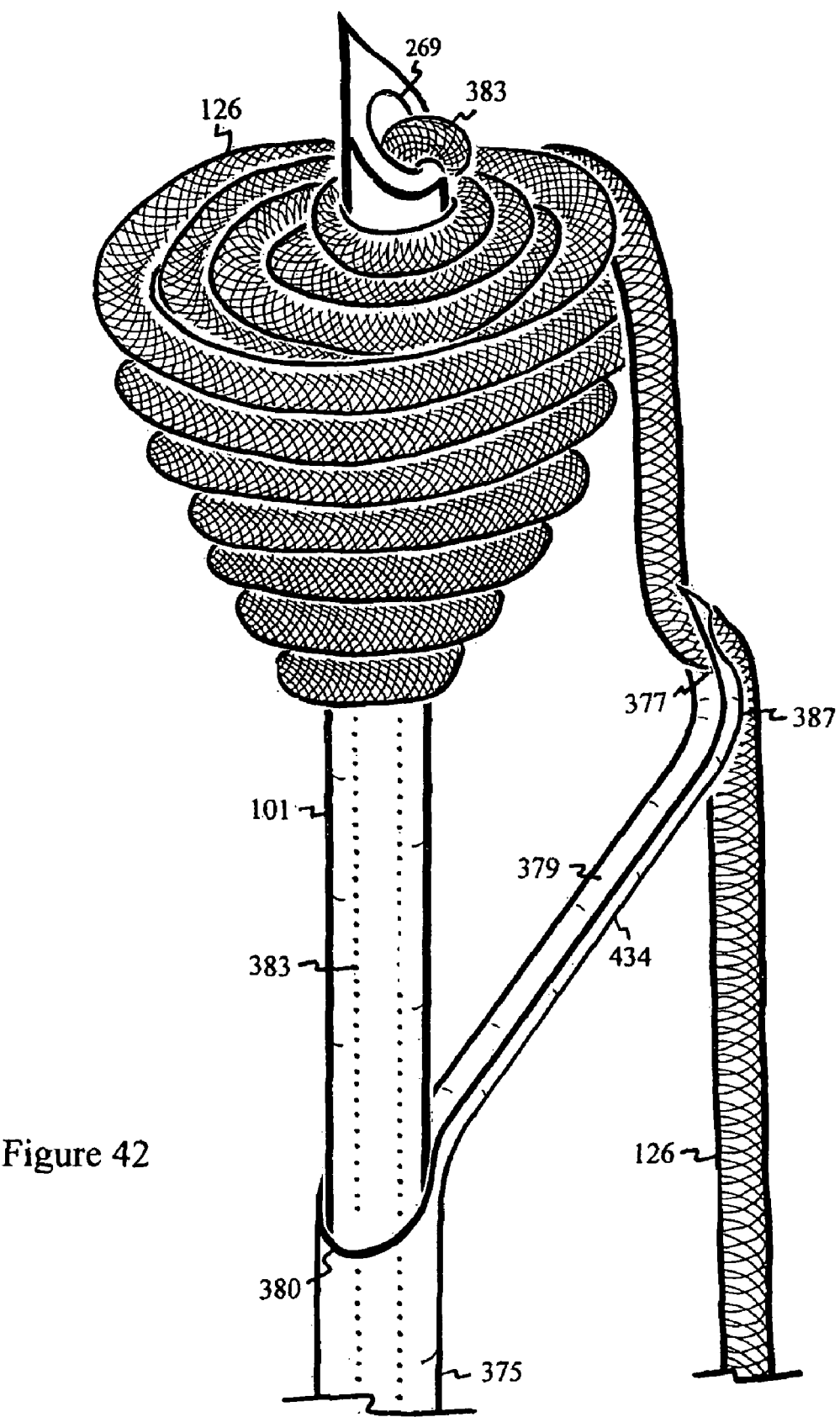
FIG. 42 shows sliding of the elastically curved extension arm 434 over the rotating needle 101 to regulate the size and shape of filament 126 spooling.

As the rotating needle 101 rotates, the beveled tip of the rotating needle 101 winds and spools the filament 126 over the shaft of the rotating needle 101, as shown in FIG. 41. The portion of the filament 383 extends into and freely spins in the lumen 269 of the rotating needle 101 during spooling. The spooled filament 126 can grow and lengthen by a gradual withdrawal of the elastic extension arm 434, as shown in FIG. 42. The bend 387 of the elastic extension arm 434 is round to minimize friction between the filament 126 and the hole 377 of the elastic extension arm 434.

Figure 43:
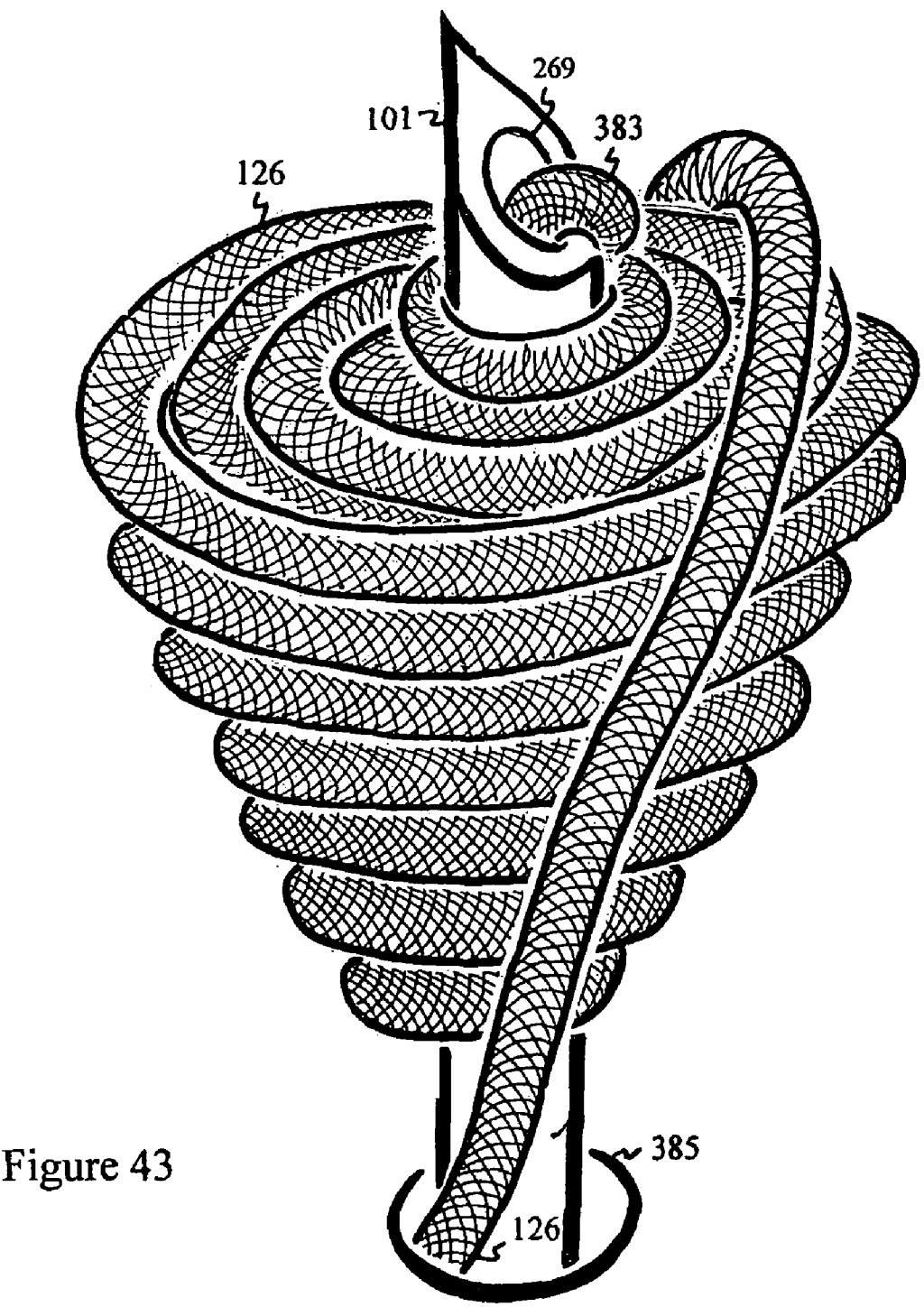
FIG. 43 shows spooled filament 126 and rotating needle 101 after withdrawal of the elastically curved extension arm 434 from the punctured hole 385.
Figure 44:
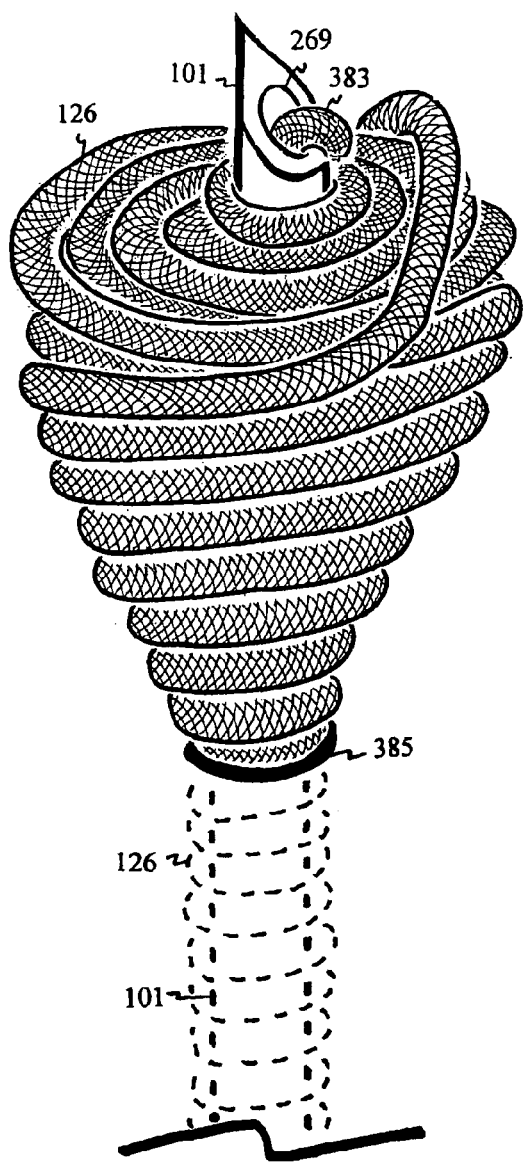
FIG. 44 shows occlusion of the punctured hole 385 by spooling the filament 126 over the rotating needle 101.
Figure 45:
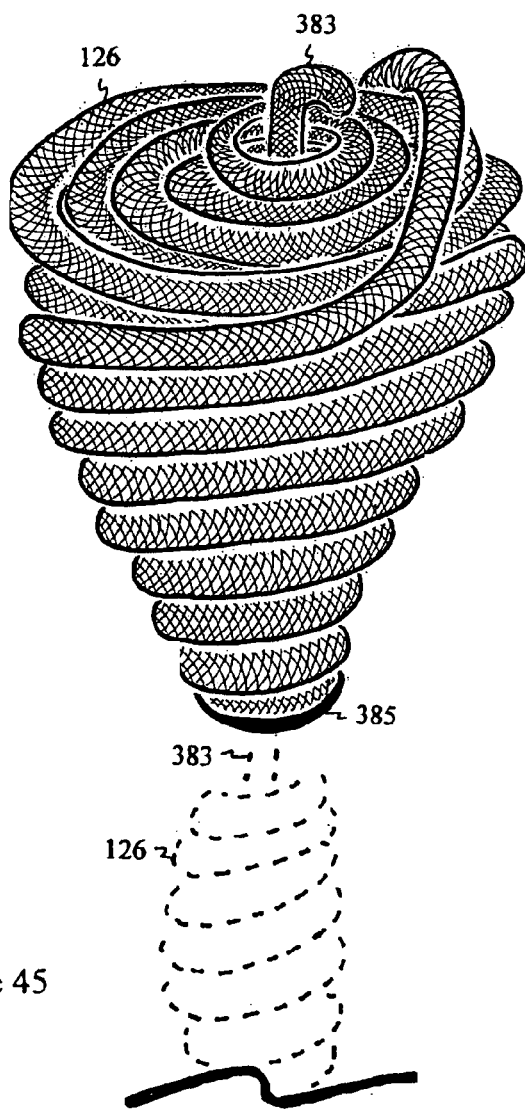
FIG. 45 shows the deployed spooled filament 126 after withdrawal of the rotating needle 101.

Spooling or bulking of filament 126 within the intervertebral disc 100 may require sealing of the hole punctured by the introducer needle 381 or rotating needle 101 to prevent leakage of nucleus pulposus 128. Before completion of spooling, the elastic extension arm 434 is withdrawn from the punctured hole 385, as shown in FIG. 43. As the rotating needle 101 continues to rotate, the filament 126 spirals over the rotating needle 101 to fill and occlude the punctured hole 385, as shown in FIG. 44. The portion of filament 383 within the lumen 269 of the rotating needle 101 spins freely. The spooled filament 126 is deployed by withdrawing the well-lubricated rotating needle 101 from tissue to occlude the punctured hole 385, as shown in FIG. 45.

Figure 46:
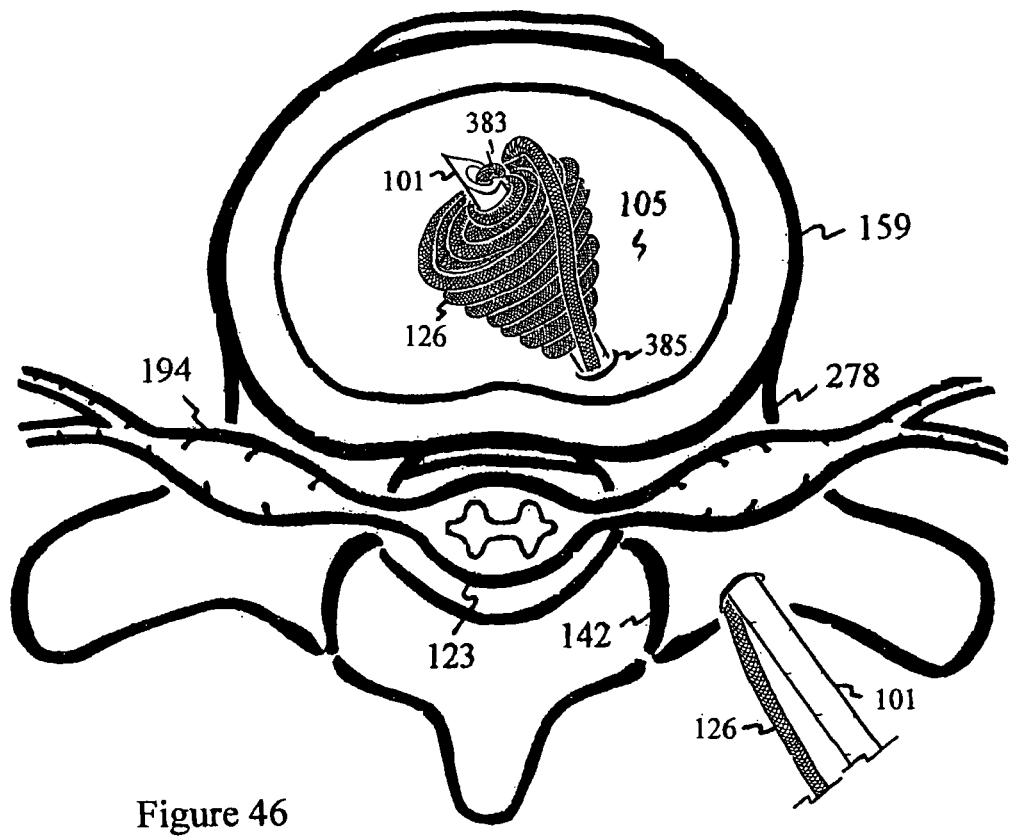
FIG. 46 shows rotating needle 101 puncture through the pedicle 278 and endplate 105 followed by spooling of the filament 126 to bulk and thicken the intervertebral disc.
Figure 47:
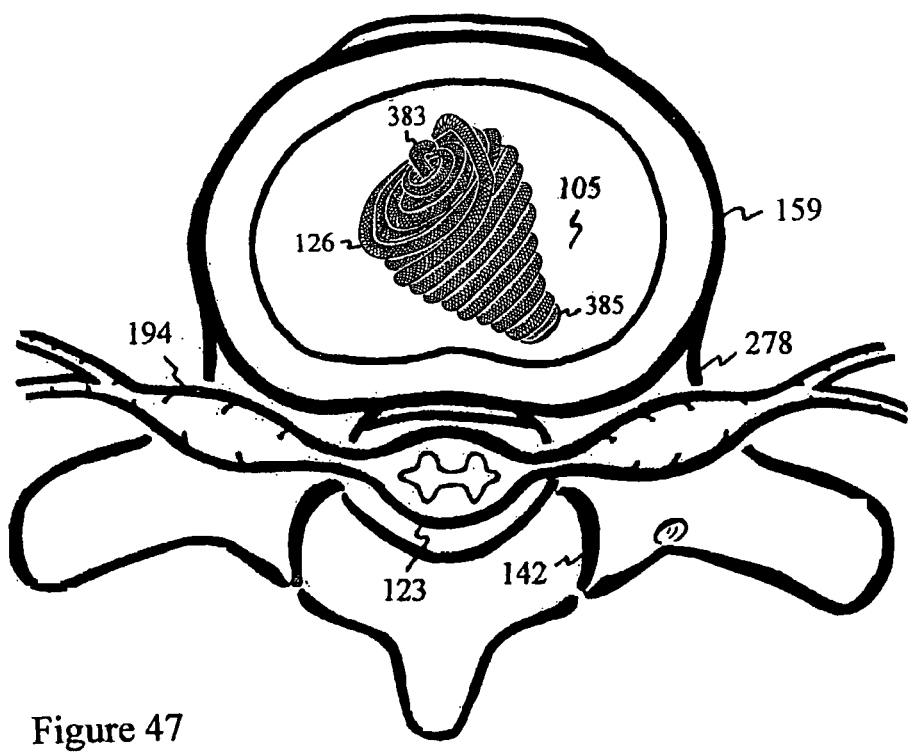
FIG. 47 shows deployment of the spooled filament 126 following the rotating needle 101 withdrawal to bulk and thicken the disc between the cartilaginous endplates 105.
Figure 48:
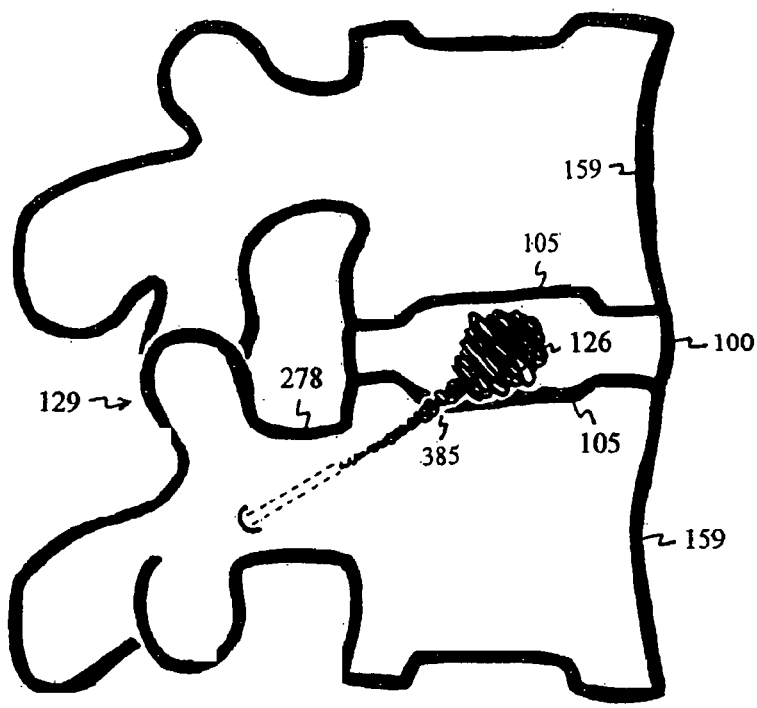
FIG. 48 shows a side view of the vertebral segment with the spool of filament 126 bulking and thickening the disc 100 and occluding the punctured hole 385.

The introducer needle 381 containing the filament 126, elastic extension arm 434 and rotating needle 101 can puncture or enter the pedicle 278 superiorly or inferiorly through the vertebral body 159 and cartilaginous endplate 105 into the intervertebral disc 100. Drilling of the pedicle 278 and cartilaginous endplate 105 may be required before insertion of the introducer needle 381. The introducer needle 381 is then withdrawn from the pedicle 278. The elastic extension arm 434 extends from the closed to open position within the intervertebral disc 100 and resumes the resilient curvature. As the rotating needle 101 rotates, the beveled tip of the rotating needle 101 winds and spools the filament 126 over the shaft of the rotating needle 101 to bulk and thicken the degenerated disc 100 between the endplates 105. The elastic extension arm 434 or elastic tube 375 is then withdrawn from the pedicle 278, as shown in FIG. 46. Additional needle 101 rotation spirals the filament 126 over the shaft of the rotating needle 101, occluding the punctured hole 385 at the cartilaginous endplate 105 to preserve hydrostatic pressure within the disc 100 and prevent leakage of nucleus pulposus. The spooled filament 126 is deployed by withdrawing the rotating needle 101, as depicted in FIG. 47. A side view of a vertebral segment at FIG. 48 shows the spool of filament 126 bulking, supporting, thickening or filling the degenerated disc 100 from within. The punctured hole 385 at the cartilaginous endplate 105 is occluded by the spiral of filament 126 to preserve hydrostatic pressure of the disc 100.

Unlike the cartilaginous endplate 105, sealing or occluding the punctured hole 385 by filament 126 spiraling is not important in other tissue. The introducer needle 381 and elastic tube 375 can be held stationary to strip or slide the spooled filament 126 off the shaft of the withdrawing rotating needle 101.

Figure 49:
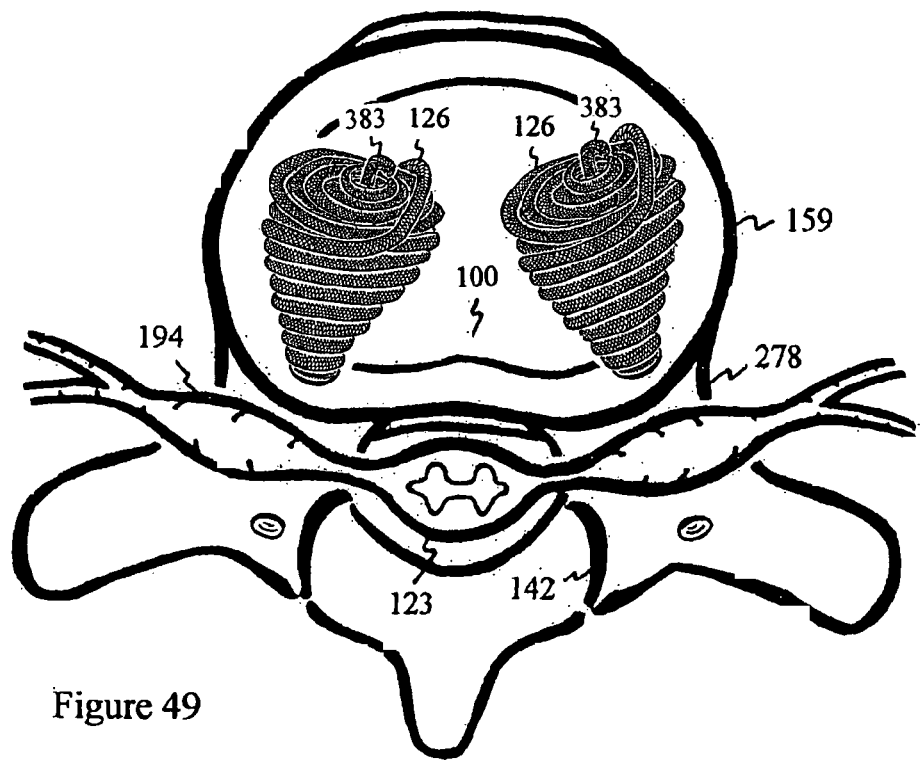
FIG. 49 shows two spools of filament 126 deployed through both pedicles 278 to sustain compressive loads upon the intervertebral disc 100.

In addition to bulking, filling and supporting from within the degenerated disc 100, material permeable to water and small molecular solutes can be selected for making the filament 126 to re-establish the exchange of nutrients and waste between the avascular disc 100 and bodily circulation. In essence, the extended spiraling filament 126 through the endplate 105 can be the disc shunt or conduit to re-establish the exchange of nutrients and waste between the avascular disc 100 and nutrients available within the vertebral body 159, as discussed in PCT/US2004/14368 filed on 7 May 2004 by J. Yeung and T. Yeung, and PCT/US2007/03194 filed on 5 Feb. 2007 by J. Yeung and T. Yeung. Spooling of filaments 126 can be done through both pedicles 278 to bulk, support and fill the degenerated disc 100 evenly, as depicted in FIG. 49, thus sustaining compressive loads and alleviating back pain. The exchange of nutrients and waste can also be expedited with two spirals of filaments 126 through the endplate 105.

Figure 50:
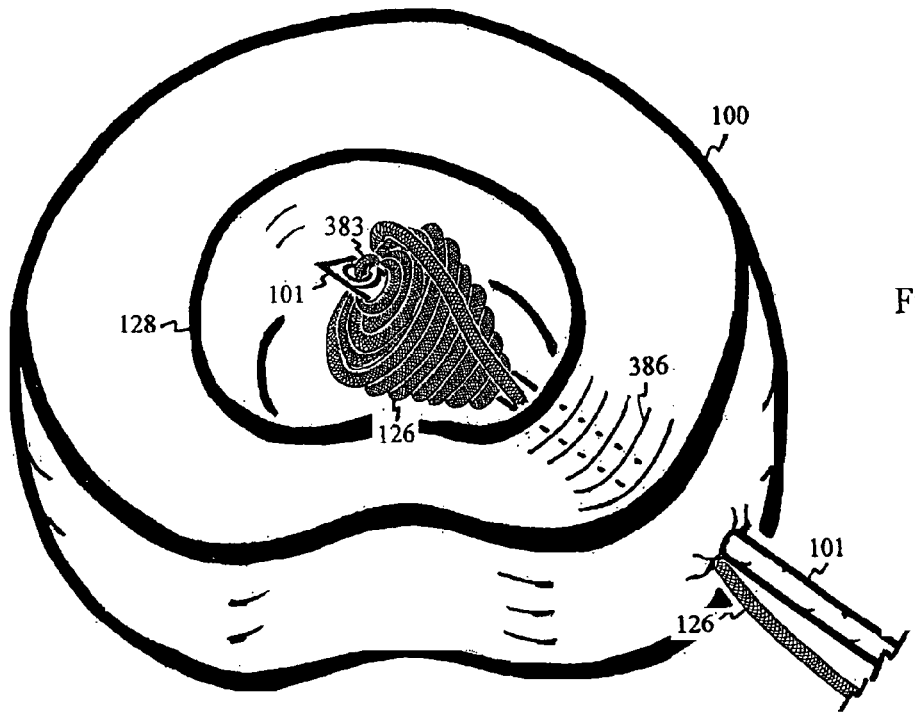
FIG. 50 shows spooled filament 126 formed after the rotating needle 101 punctured into the annulus 386.
Figure 51:
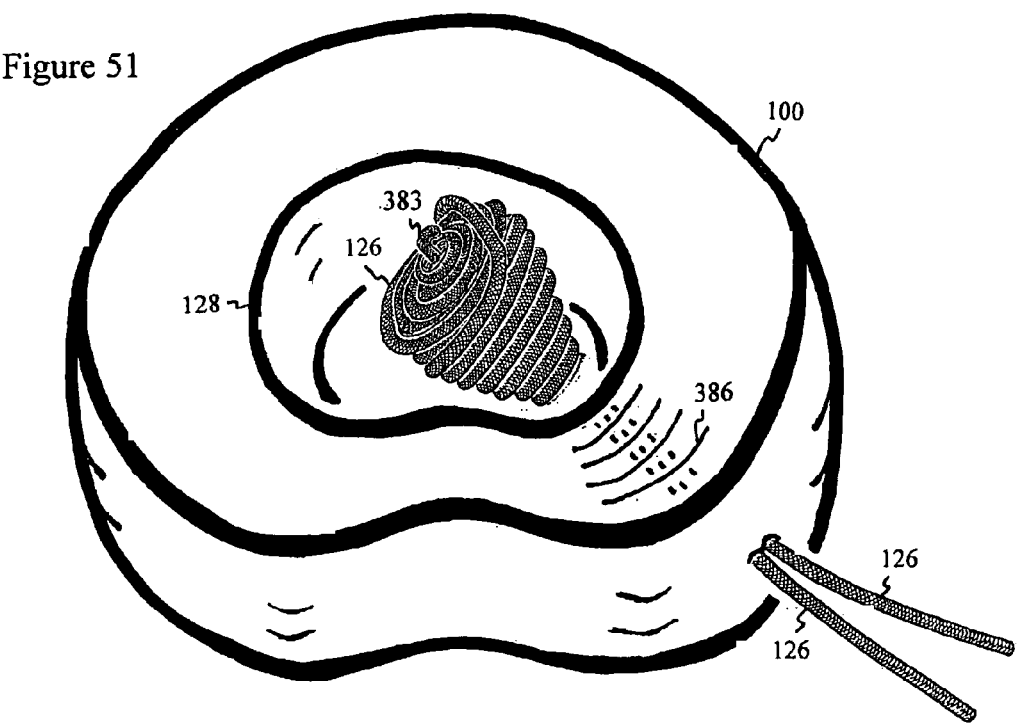
FIG. 51 shows the deployed spool of filament 126 following withdrawal of the rotating needle 101 to bulk and thicken the disc 100.

The intervertebral disc 100 is also accessible using fluoroscopic guidance. The rotating needle 101 can also puncture or enter directly into the disc 100 through layers of annulus 386 and spool the filament 126 to bulk, support and thicken the disc 100, as shown in FIG. 50. The deployed spooled filament 126 bulks and supports the degenerated disc 100, as shown in FIG. 51 to alleviate back pain by reducing spinal instability and stress on the facet joints. In addition, the proximal end of the filament 126 extends beyond the disc 100. By using permeable material, the extended filament 126 from the disc 100, as shown in FIG. 51, can re-establish the exchange of nutrients and waste between the avascular disc 100 and bodily circulation. As a result, the degenerated disc 100 may regenerate for long-term pain relief.

Figure 52:
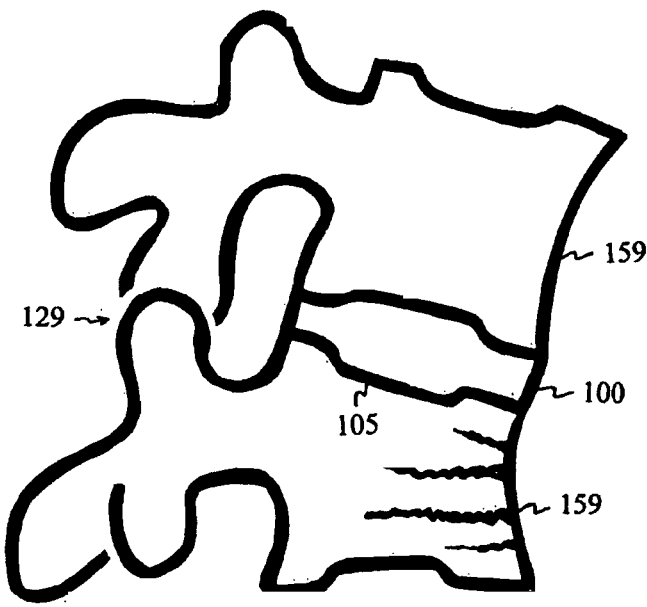
FIG. 52 shows a fractured or compressed osteoporotic vertebral body 159.
Figure 53:
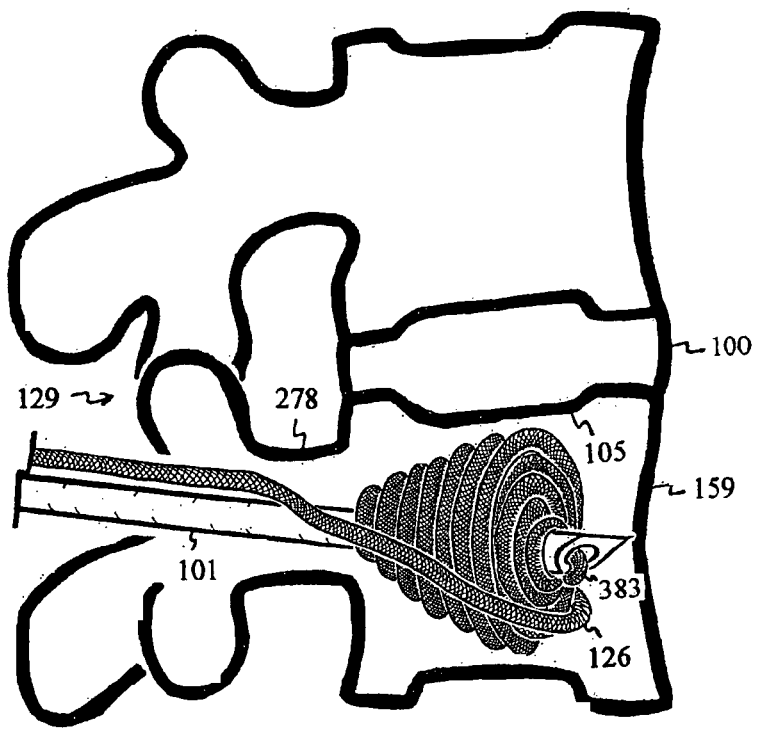
FIG. 53 shows rotating needle 101 punctured through the pedicle 278, then the spooled filament 126 or wire re-expands, bulks or repairs the fractured vertebral body 159.
Figure 54:
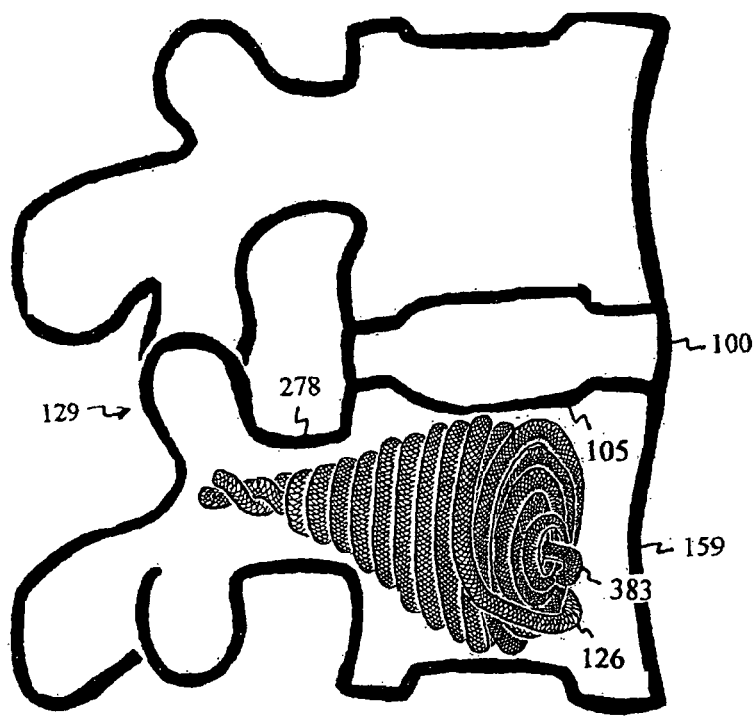
FIG. 54 shows the spool of filament 126 or wire deployed by withdrawing the rotating needle 101 to bulk and support the previously compressed vertebral body 159.
Figure 55:
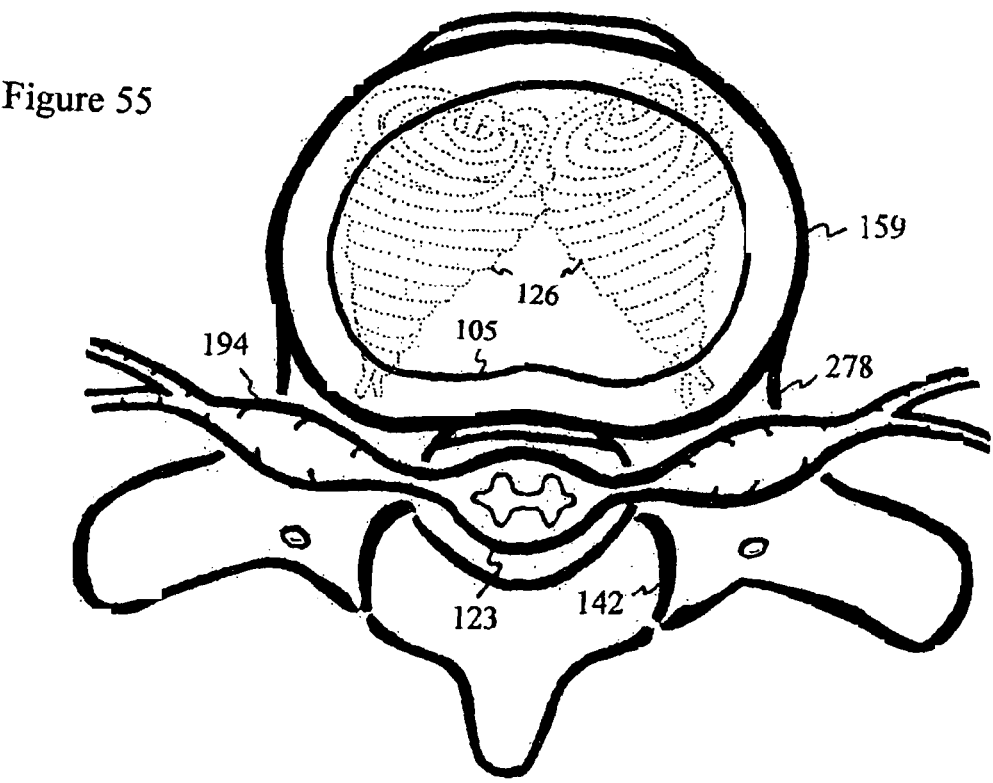
FIG. 55 shows the top view of the vertebral body 159 with two spools of filament 126.

Vertebral fractures, as shown in FIG. 52, are common among osteoporotic patients. The compressed vertebral body 159 is painful and disfiguring. The rotating needle 101 and filament 126 enter through the pedicle 278 and spool the filament 126 to expand, fill, support and/or restore the vertebral body 159, as shown in FIGS. 53-54. Two spools of filament 126 can be implanted through both pedicles 278 to fill the vertebral body 159, as depicted in FIG. 55. For high-tension spooling, the filament 126 can be a surgical wire or cable to restore the compressed vertebral body 159. As a result, normal posture can be restored, and pain alleviated. Unlike bone cement injections, restoring the vertebral body 159 by spooling filament 126 is not pressure related and is unlikely to encroach upon the nerve root or spinal cord.

Spooled filament 126 can also be used in conjunction with bone cement. After expansion or restoration of the vertebral body 159 by spooling filament 126, bone cement or other solidifying elements can be infused or injected over the spool of filament 126 to fortify, immobilize and/or restore the vertebral body 159 without using high pressure and high risk injections.

Figure 56:
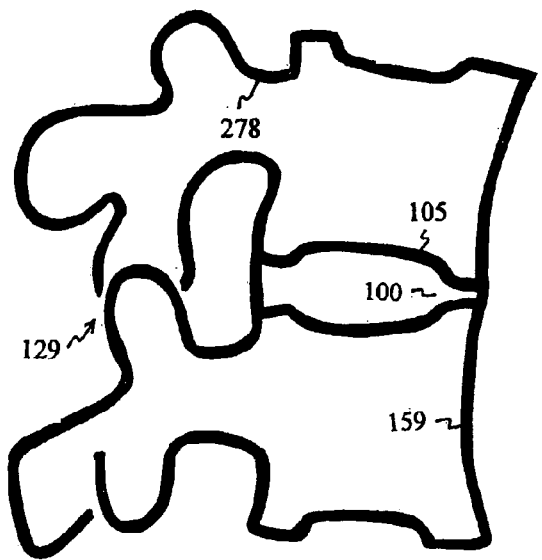
FIG. 56 shows an anteriorly thin disc 100 leading to kyphosis.
Figure 57:
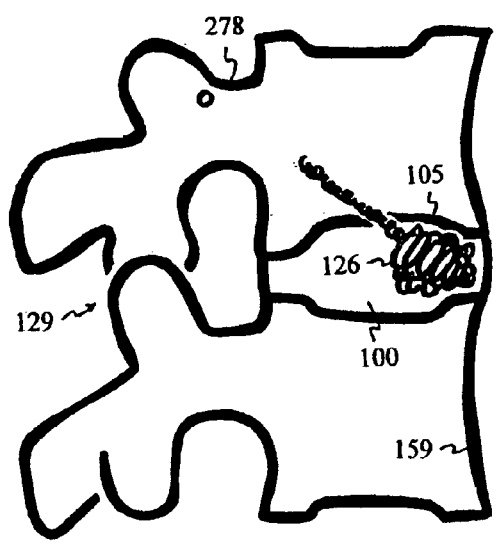
FIG. 57 shows selective bulking and thickening in the anterior portion of the disc 100 using a spool of filament 126 to correct kyphosis.

Thinning of the anterior disc 100 can lead to kyphosis, as shown in FIG. 56, displaying a forward leaning posture. A filament 126 with the spooling device can be introduced through the pedicle 278 and selectively spooled in the anterior portion to restore disc 100 height, as shown in FIG. 57. Similarly, the filament 126 and the spooling device can also enter directly into the disc 100 through the sidewall to selectively spool and thicken the kyphotic disc 100.

Figure 58:
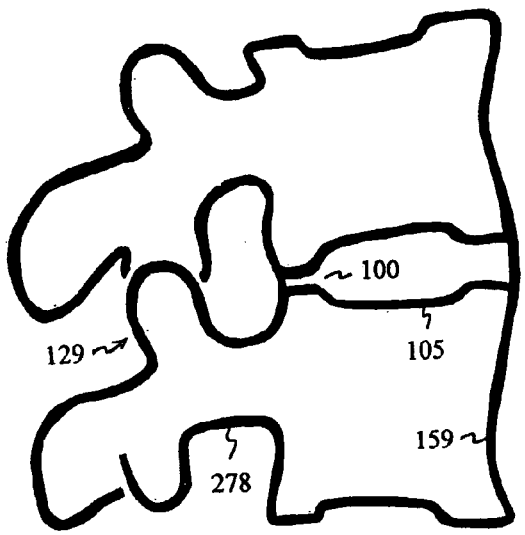
FIG. 58 shows a posteriorly thin disc 100 leading to lordosis.
Figure 59:
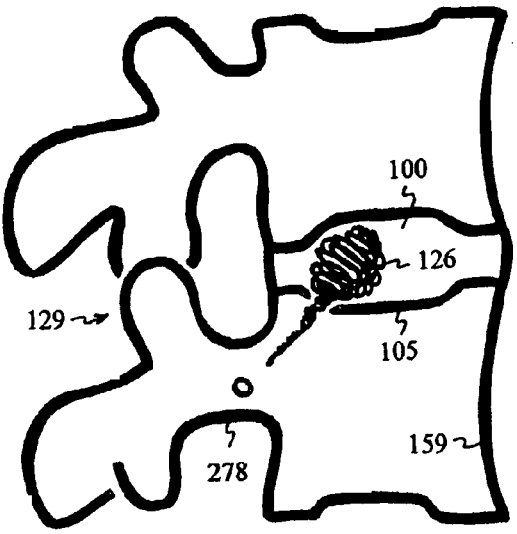
FIG. 59 shows selective bulking and thickening in the posterior portion of the disc 100 using a spool of filament 126 to correct the lordosis.

Thinning of the posterior disc 100 can lead to lordosis, as shown in FIG. 58, displaying a swayback posture. A filament 126 with the spooling device can be introduced through the pedicle 278 and selectively spooled in the posterior portion to restore height of the disc 100, as shown in FIG. 59. Similarly, the filament 126 and the spooling device can also enter directly into the disc 100 through the sidewall to selectively spool within the thin posterior portion of the disc 100.

Figure 60:
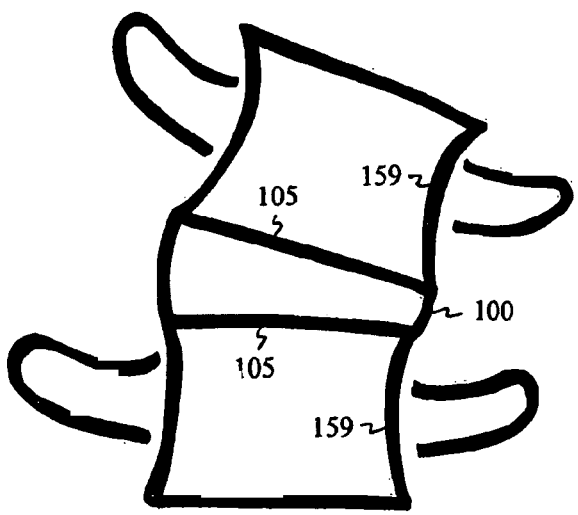
FIG. 60 shows lateral thinning of the intervertebral disc 100 leading to scoliosis.
Figure 61:
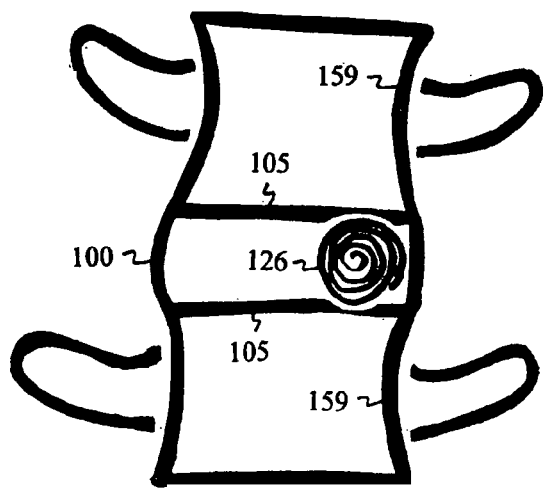
FIG. 61 shows selective bulking and thickening in the lateral portion of the disc 100 using a spool of filament 126 to correct scoliosis.

Lateral thinning of the disc 100 can lead to scoliosis, as shown in FIG. 60. A filament 126 with the spooling device can be introduced through the pedicle 278 or the disc 100 to selectively bulk and thicken the thin section of the disc 100. As a result, scoliosis is minimized or corrected through minimally invasive spooling of the filament 126, as depicted in FIG. 61.

Figure 62:
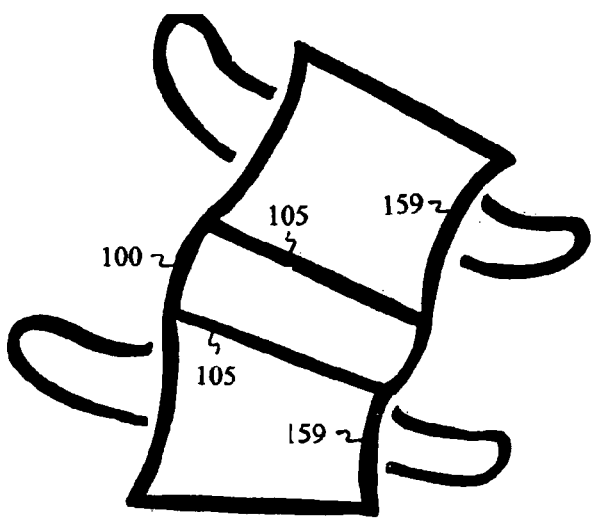
FIG. 62 shows lateral thinning of the vertebral body 159 leading to scoliosis.
Figure 63:
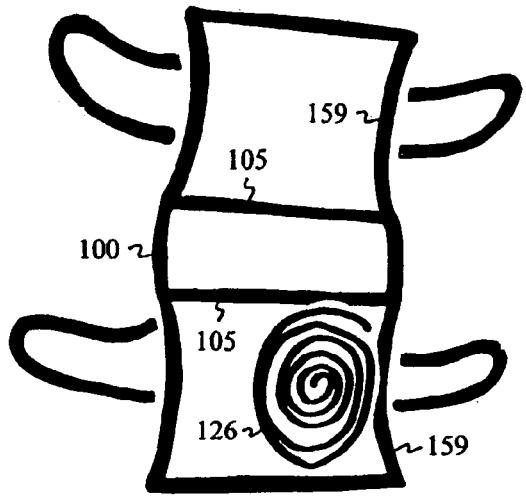
FIG. 63 shows selective bulking and thickening in the lateral portion of the vertebral body 159 using a spool of filament 126 or wire to correct the scoliosis.

Lateral thinning of the vertebral body 159 can also contribute to scoliosis, as shown in FIG. 62. A filament 126 with the spooling device can be introduced through the pedicle 278 to selectively bulk and thicken the thin portion of the vertebral body 159. As a result, scoliosis is minimized or corrected through minimally invasive spooling of the filament 126, as depicted in FIG. 63.

Figure 64:
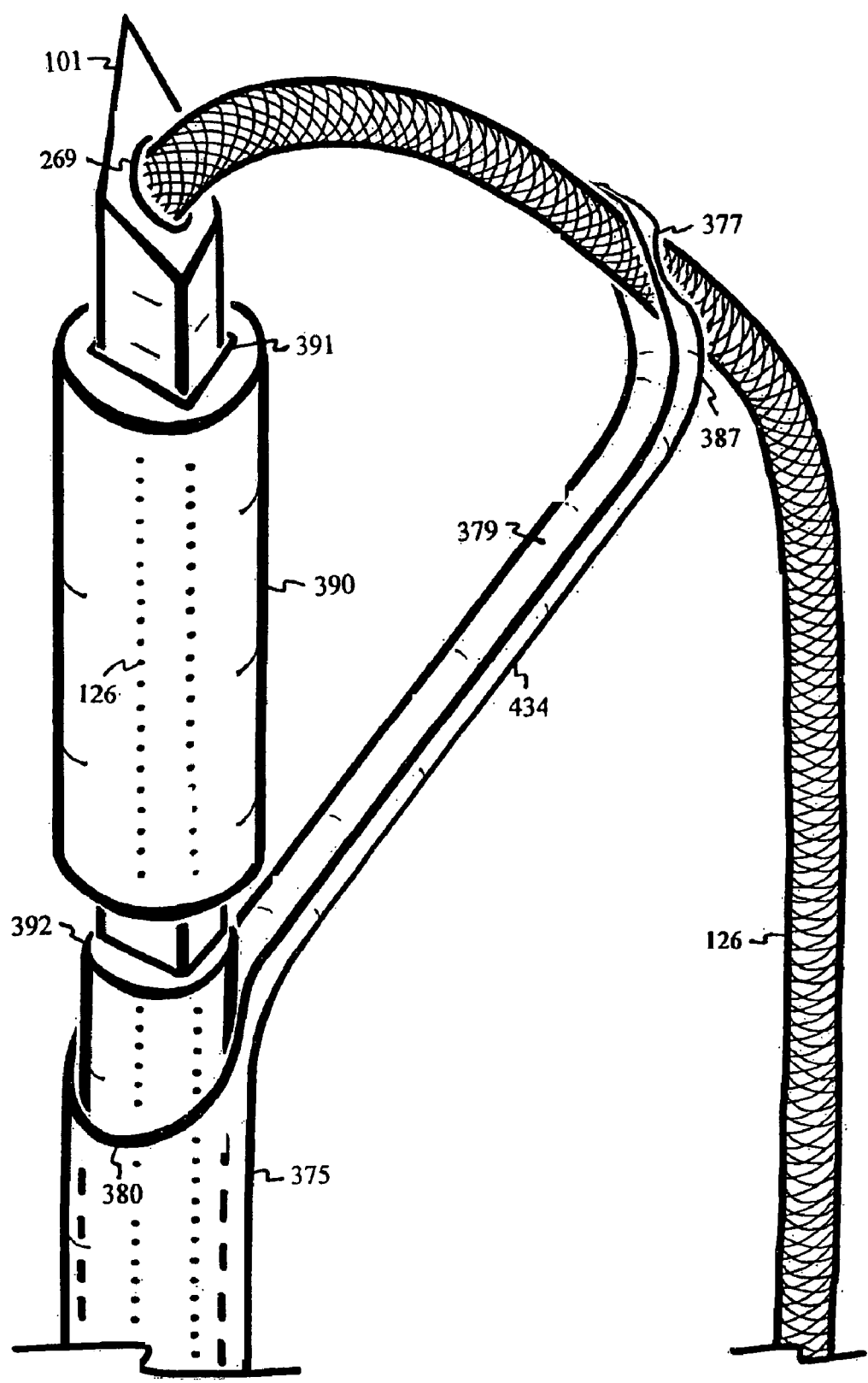
FIG. 64 shows a spindle 390 for spooling filament 126 directed by the extension arm 434.
Figure 65:
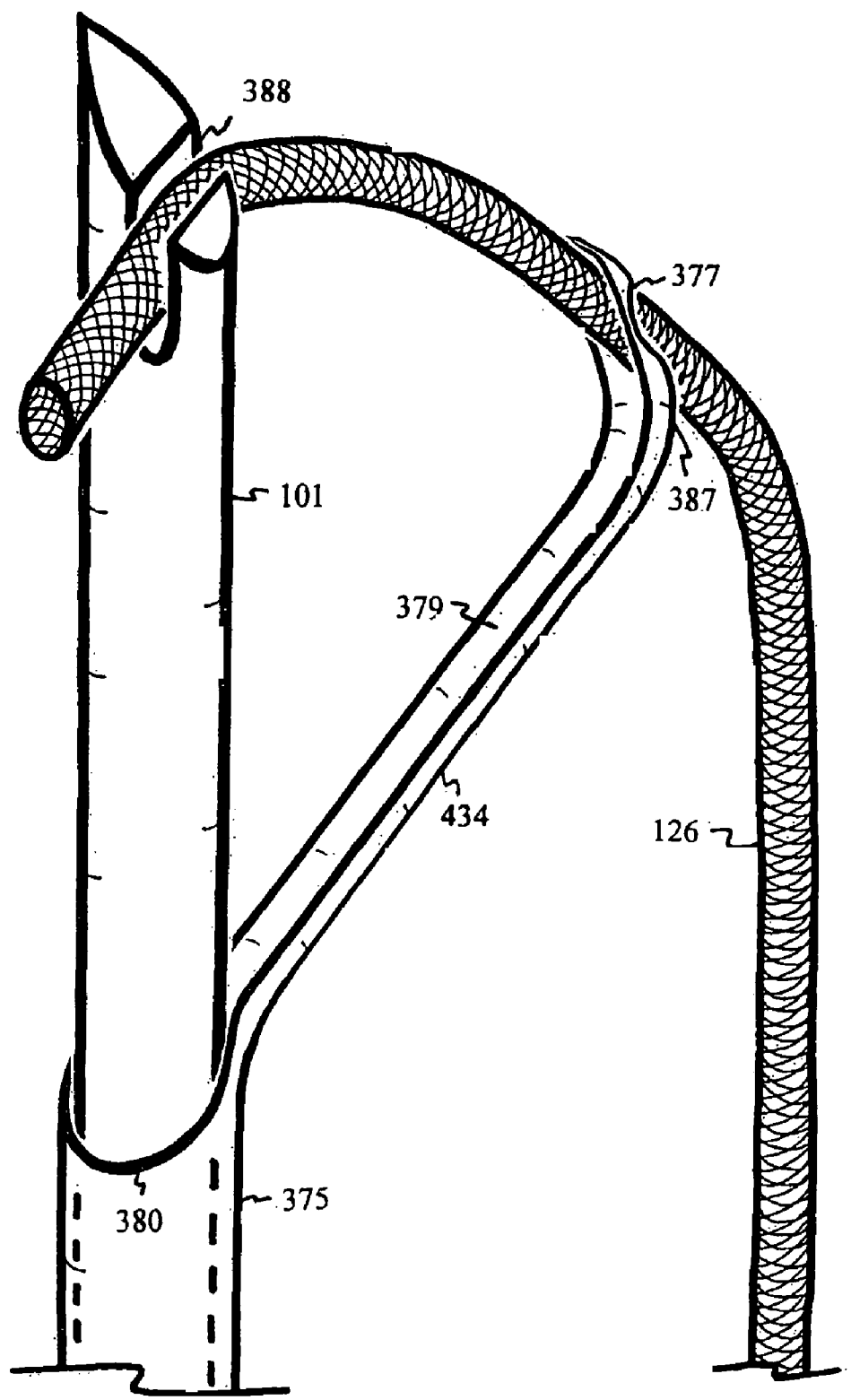
FIG. 65 shows filament 126 anchoring within a slit 388 at the distal end of the rotating needle 101.
Figure 66:
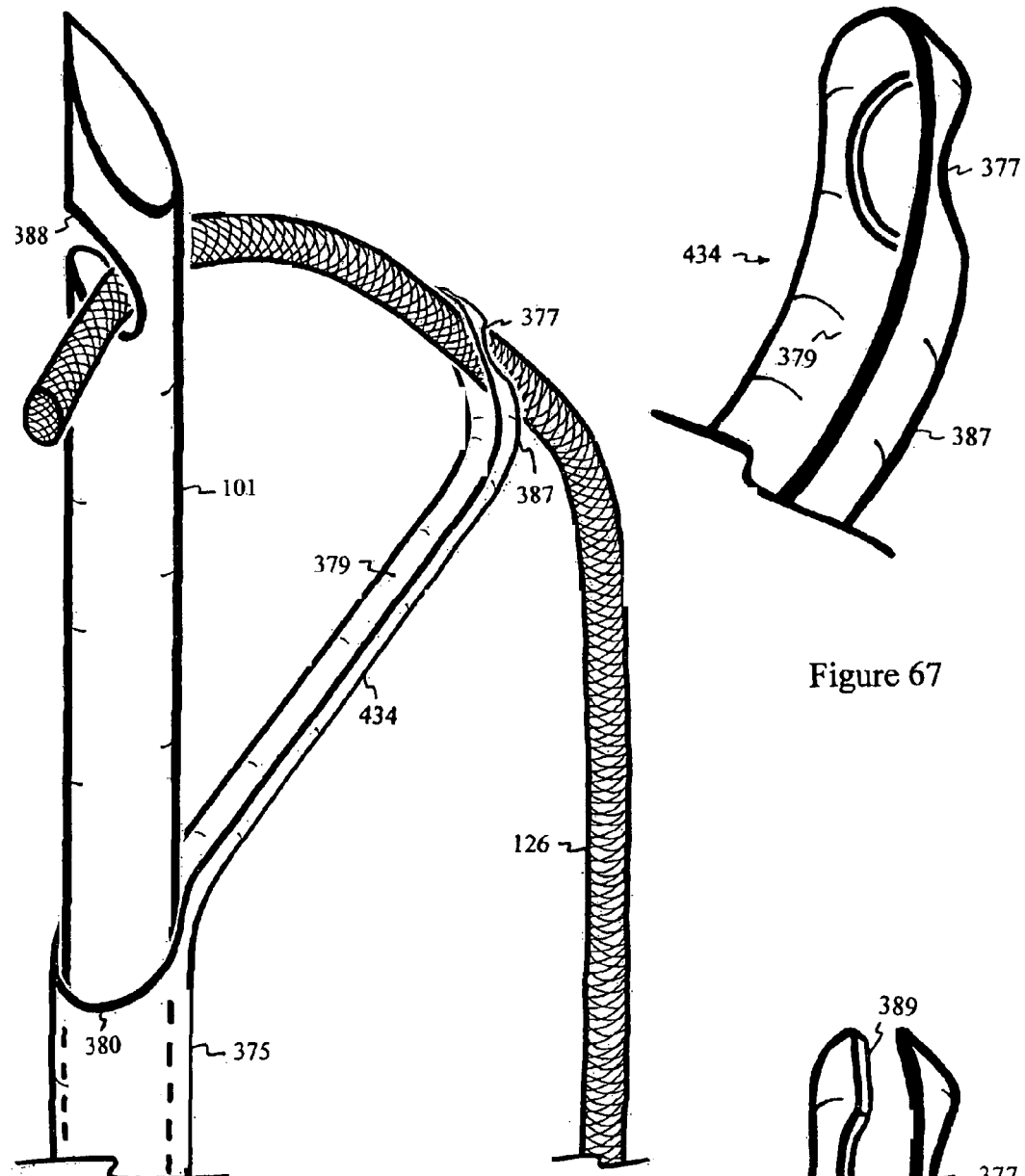
FIG. 66 shows filament 126 anchoring within a slanted slit 388 at the side of the rotating needle 101.

A combination or substitution of spooling devices can be used. A spindle 390 can be used to spool the filament 126 directed or guided by an extension arm 434, as shown in FIG. 64. The distal portion of the rotating needle 101 can contain a slit 388 for holding or anchoring the filament 126, as shown in FIG. 65. Upon completion of spooling, the distally opened slit 388 allows deployment of the spool of filament 126 during rotating needle 101 withdrawal. A slanted slit 388 can be at the side of the rotating needle 101 with the slant toward the distal end, as shown in FIG. 66. The slanted orientation may allow deployment of the spool of filament 126 upon withdrawal of the rotating needle 101.

Figure 67:
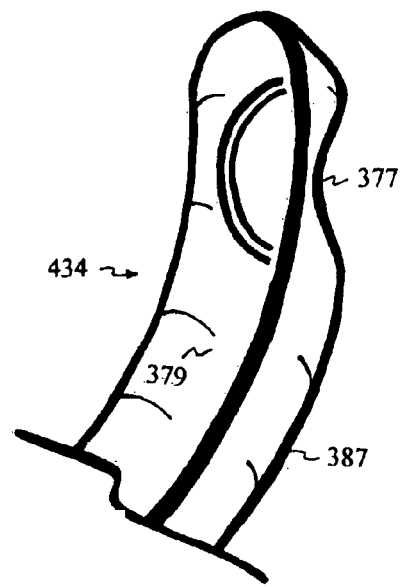
FIG. 67 shows the distal end of the extension arm 434.
Figure 68:
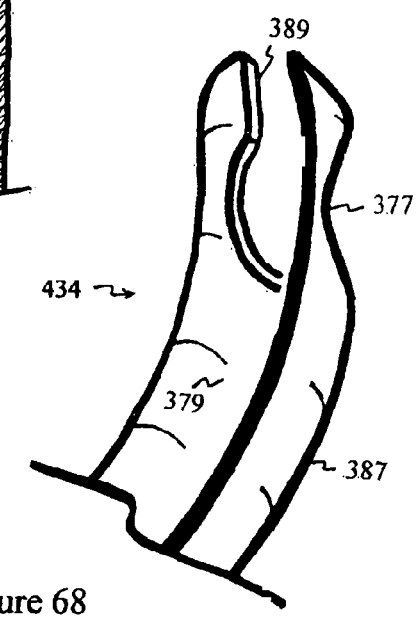
FIG. 68 shows an open slit 389 into the hole 377 of the extension arm 434.

The distal portion of the elastic tube 375 can be cut or machined to form the elastic extension arm 434, as shown in FIG. 33. The lumen 379 of the elastic tube 375 becomes a trough 379 of the elastic extension arm 434, as shown in FIG. 67. The hole 377 of the elastic extension arm 434 can have a slit 389, as shown in FIG. 68, to facilitate withdrawal from the filament 126 prior to having the filament 126 spiral over the shaft of the rotating needle 101 to occlude the punctured hole 385.

Figure 69:
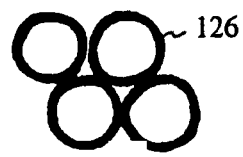
FIG. 69 shows stacking of filament 126 with round cross-sections within a spool.
Figure 70:
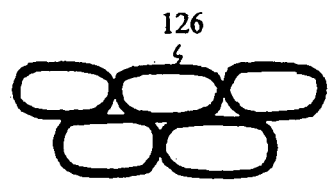
FIG. 70 shows stacking of filament 126 with elongated cross-sections within a spool.
Figure 71:
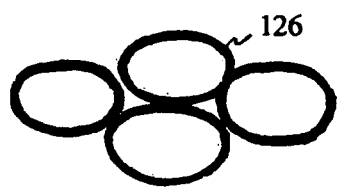
FIG. 71 shows stacking of filament 126 with oval cross-sections within a spool.
Figure 72:
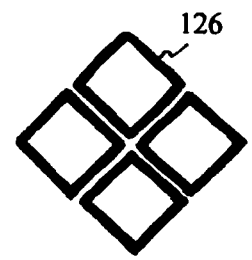
FIG. 72 shows stacking of filament 126 with square cross-sections within a spool.
Figure 73:
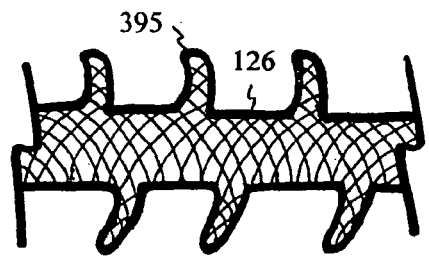
FIG. 73 shows protrusions 395 from a filament 126.
Figure 74:
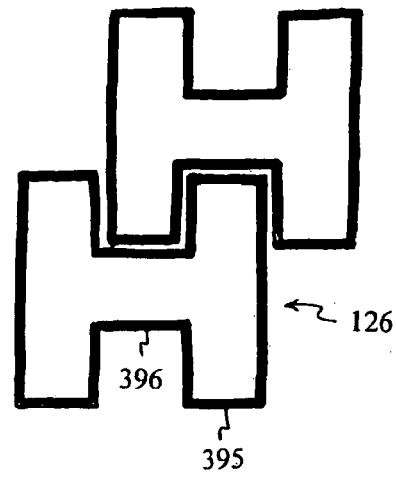
FIG. 74 shows connection between indentations 396 and protrusions 395 to link and solidify stacking between portions of the filament 126 within a spool.

The cross-sectional configuration of the filament 126 can affect rigidity, durability, mobility or stability of the spool within tissue. FIG. 69 shows stacking of filament 126 with round cross-sections. The round cross-sections stack reasonably well without excessive sliding between layers of spooled filament 126. Filament 126 with round cross-sections may be suitable within the bladder neck to treat stress urinary incontinence. FIG. 70 shows stacking of filament 126 with elongated and round-cornered cross-sections. The elongated cross-sections can slide between layers of spooled filament 126. Filament 126 with elongated cross-sections may be suitable for cosmetic corrections, such as shallow wrinkles. Physicians can massage, flatten, smooth out or partially disperse the spool of filament 126 to conform to the contour of the skin. Collagen and hyaluronate will eventually grow and fill in and around the filament 126 for a long lasting cosmetic correction. FIG. 71 shows stacking of filament 126 with oval cross-sections. Filament 126 with oval cross-section stacks better than filament 126 with elongated cross-section. The oval cross-sectioned filament 126 may be suitable for correcting deep wrinkles since the spooled filament 126 has better stability. FIG. 72 shows stacking of filament 126 with square cross-sections. The filament 126 with square cross-sections stacks well, providing stability within the spooled filament 126. Spooling of the square cross-sectioned filament 126 may have the stability or durability for bulking and cushioning within the degenerated disc 100. FIG. 73 shows protrusions 395 from the filament 126. The protrusions 395 from the filament 126 may help to tie, link, anchor, fasten or connect multiple layers of the filament 126 within a spool for stability. The filament 126 with protrusions 395 may be suitable for restoring the osteoporotic vertebral body 159. FIG. 74 shows a filament 126 with cross-sections containing protrusions 395 and indentations 396. The protrusions 395 are sized and configured to fit within indentations 396 as a tongue and groove locking mechanism. The locking mechanism provides connections and linkages between layers within the spooled filament 126. Hence, the filament 126 containing protrusions 395 and indentations 396 may maintain shape well. It may also be suitable for restoring the osteoporotic vertebral body 159.

The filament 126 can be formed by extruding, molding, braiding, weaving, coiling, spiraling or machining. The filament 126 can also be called or classified as a wire, shunt, conduit, wick, tube or suture.

A wide range of non-degradable materials can be used to fabricate the filament 126. The filament 126 can be metallic, such as stainless steel or titanium. Biocompatible polymers, such as Nylon, polytetrafluoroethylene, polypropylene, polyethylene, polyamide, polyester, polyurethane, silicone, polyether-ether-ketone, acetal resin, polysulfone, polycarbonate, hyaluronate, alginate, cotton, or linen are possible candidates. Fiberglass can also be a part of the filament 126 to provide capillarity for transporting nutrients and waste for the avascular disc 100.

For investigative purposes, a biodegradable filament 126 may show treatment efficacy within weeks or months. Since the filament 126 degrades within months, any unforeseen adverse outcome would be nullified or negated. If the investigative-degradable filament 126 shows efficacy, a permanent or non-degradable filament 126 can then be installed to provide continuous treatment or benefits. The biodegradable filament 126 can be made with polylactate, polyglycolic, polylactide-co-glycolide, polycaprolactone, trimethylene carbonate, silk, catgut, collagen, poly-p-dioxanone or combinations of these materials. Other degradable polymers, such as polydioxanone, polyanhydride, trimethylene carbonate, poly-beta-hydroxybutyrate, polyhydroxyvalerate, poly-gama-ethyl-glutamate, poly-DTH-iminocarbonate, poly-bisphenol-A-iminocarbonate, poly-ortho-ester, polycyanoacrylate or polyphosphazene can also be used.

Part of the filament 126 can include but is not limited to one of the following materials, carboxymethyl cellulose, cellulose acetate, cellulose sulfate, cellulose triacetate, chitin, chitosan, chloroprene, ethylene-vinyl acetate, fluoro-silicon hydrogel, hyaluronan, hyaluronate, neoprene, polyacrylamide, polyacrylate, polyamide, polyacrylonitrile, poly-butylene terephthalate, poly-dimethyl-siloxane, poly-hydroxy-ethyl-acrylate, poly-hydroxy-ethyl-methacrylate, poly-hydroxy-methyl methacrylate, polymethacrylate, polymethylmethacrylate, polypropylene oxide, poly-siloxane, polyvinyl alcohol, poly-vinylpyrrolidone, silanol and vinyl methyl ether.

The rotating needle 101, elastically curved tube 375 and introducer needle 381 can be made with stainless steel, titanium, nickel-titanium or other alloy. The rotating needle 101, elastically curved tube 375 and introducer needle 381 can be marked with penetration markers or coated with lubricant, analgesic, antibiotic, radiopaque, echogenic or MRI visible agent.

The disc 100 containing a filament 126 extending through the annulus or endplate can be called the shunted disc 100. Hydrostatic pressure within the shunted disc 100 can be further preserved by a swellable coating over the filament 126 to seal the gap between the filament 126 and annulus or between the filament 126 and endplate 105. The swellable coating can be polyethylene glycol, crosslinked polyethylene glycol, polyurethane, swellable or elastic materials.

Sodium carbonate, sodium bicarbonate, potassium carbonate, potassium bicarbonate, magnesium carbonate, calcium carbonate, barium carbonate, potassium phosphate, sodium phosphate or other buffering agent can be loaded in or coated on the filament 126 to neutralize lactic acid and spontaneously alleviate pain caused by acid irritation from the disc 100.

Similarly, magnesium oxide, magnesium hydroxide, sodium hydroxide, potassium hydroxide, barium hydroxide, cesium hydroxide, strontium hydroxide, calcium hydroxide, lithium hydroxide, rubidium hydroxide, neutral amines or other alkaline agent can be loaded in or coated on the filament 126 to neutralize lactic acid and spontaneously alleviate back pain caused by acid irritation.

In addition, an initial supply of nutrients, such as sulfate, glucose, glucuronic acid, galactose, galactosamine, glucosamine, hydroxylysine, hydroxylproline, serine, threonine, chondroitin sulfate, keratan sulfate, hyaluronate, magnesium trisilicate, magnesium mesotrisilicate, magnesium oxide, Magnosil, Pentimin, Trisomin, orthosilicic acid, magnesium trisilicate pentahydrate, Serpentine, sodium metasilicate, silanolates, silanol group, sialic acid, silicic acid, boron, boric acid, minerals and/or other amino acids can be used to coat or load the filament 126 as additives to enhance or initiate the production of sulfated glycosaminoglycans and collagen within the degenerative disc 100. Growth factor, antibiotic or analgesic may also be helpful to load into or coat on the filament 126.

Fibrous formation over the filament 126 may affect the exchange of nutrients and waste between the disc 100 and bodily circulation. Immuno inhibitor can be coated over and/or incorporated into the filament 126 to minimize fibrous formation or tissue response. Examples of immuno inhibitors include, but are not limited to: actinomycin-D, aminopterin, azathioprine, chlorambucil, corticosteroids, crosslinked polyethylene glycol, cyclophosphamide, cyclosporin A, 6-mercaptopurine, methylprednisolone, methotrexate, niridazole, oxisuran, paclitaxel, polyethylene glycol, prednisolone, prednisone, procarbazine, prostaglandin, prostaglandin $E_1$, sirolimus, steroids, other immune suppressant drugs or other immune suppressant coatings.

The filament 126 can be loaded or coated with a calcium channel blocker to minimize calcification, mineralization or blockade of the filament 126 at the cartilaginous endplate 105. The calcium channel blocker can also disperse from the filament 126 to prevent formation of calcified layers of the endplate 105. The calcium channel blocker can be one of the dihydropyridines, phenylalkylamines, benzothiazepines or others. The calcium channel blocker for loading into the filament 126 can be Amlodipine, Felodipine, Isradipine, Lacidipine, Lercanidipine, Nicardipine, Nifedipine, Nimodipine, Nisoldipine, Verapamil, Diltiazem or other calcium channel blocker.

The filament 126 can be loaded or coated with a chelating agent to minimize calcification, mineralization or blockade of the filament 126. The chelating agent can also disperse from the filament 126 to extract calcium ion, opening calcified layers of the cartilaginous endplate 105 to enhance diffusion of nutrients and waste between the disc 100 and bodily circulation. The chelating agent can be ethylene diamine tetra acetate, diethylene triamine penta acetate, meso-2,3-dimercapto succinic acid, desferoxamine, 2,3-dimercapto-1-propane sulfonate, D-penicillamine, defarasirox, dimercaprol, N,N-bis (carboxymethyl) glycine, morpholine dithiocarbamate, tetra ammonium ethylene diamine diacetic acid dithiocarbamate, ammonium diethanolamine dithiocarbamate, sodium diethyl dithio carbamate, N-benzyl-D-glucamine dithio carbamate, alpha lipoic acid, tartaric acid, glutathione, methionine and/or L-arginine. In general, the chelating agent used on or in the filament 126 can contain a carboxylated group, amine group or thiol group. Sodium or potassium carboxylate is preferred to minimize acidic irritation during extraction of calcium ion from the calcified endplate 105.

The filament 126 may have pore sizes ranging from 301 μm to 1 nm. The filament 126 may also have a length-wise gradient of various pore sizes to limit permeability. The pore sizes of the permeable gradient of the filament 126 can range from 301 μm, 100 μm, 50 μm, 10 μm, 1 μm, 700 nm, 500 nm, 300 nm, 100 nm, 50 nm, 30 nm, 10 nm, 5 nm to 1 nm to prevent infiltration of IgA, IgD, IgE, IgG, IgM, cytokines or other initiators triggering an immune reaction to the disc 100.

In addition, the filament 126 may have sections containing different pore sizes to create regions of size exclusion or permeabilities along the filament 126. The pore sizes of the filament 126 may decrease toward the section near the nucleus pulposus 128 to minimize immune responses to the nucleus pulposus 128 without excluding large nutrients from coming into or metabolites from going out of the middle portion of the annulus. Hence, the filament 126 can have permeable regions ranging from 200000, 100000, 70000, 50000, 30000, 10000, 5000, 3000, 1000, 700, 400 to 200 grams per mole of solutes.

Healthy intervertebral discs 100 are avascular and immuno-isolated. To ensure avascular and immuno-isolated conditions, the filament 126 can be incorporated, coated or partially coated with an anti-angiogenic compound. Examples of anti-angiogenic compounds include, but are not limited to, Marimastat from British Biotech [a synthetic inhibitor of matrix metalloproteinases (MMPs)], Bay 12-9566 from Bayer (a synthetic inhibitor of tumor growth), AG3340 from Agouron (a synthetic MMP inhibitor), CGS 27023A from Novartis (a synthetic MMP inhibitor), COL-3 from Collagenex (a synthetic MMP inhibitor, TETRACYCLINE® derivative), Neovastat from Aeterna, Sainte-Foy (a naturally occurring MMP inhibitor), BMS-275291 from Bristol-Myers Squib (a synthetic MMP inhibitor), TNP-470 from TAP Pharmaceuticals, (a synthetic analogue of fumagillin; inhibits endothelial cell growth), Thalidomide from Celgene (targets VEGF, bFGF), Squalamine from Magainin Pharmaceuticals (extract from dogfish shark liver; inhibits sodium-hydrogen exchanger, NHE3), Combretastatin A-4 (CA4P) from Oxigene, (induction of apoptosis in proliferating endothelial cells), Endostatin collagen XVIII fragment from EntreMed (an inhibitor of endothelial cells), Anti-VEGF Antibody from Genentech [monoclonal antibody to vascular endothelial growth factor (VEGF)], SU5416 from Sugen (blocks VEGF receptor signaling), SU6668 from Sugen (blocks VEGF, FGF, and EGF receptor signaling), PTK787/ZK 22584 from Novartis (blocks VEGF receptor signaling), Interferon-alpha (inhibitor of bFGF and VEGF production), Interferon-alpha (inhibitor of bFGF and VEGF production), EMD121974 from Merck, KcgaA (small molecule blocker of integrin present on endothelial cell surface), CAI from NCI (inhibitor of calcium influx), Interleukin-12 from Genetics Institute (up-regulation of interferon gamma and IP-10), IM862 from Cytran, Avastin, Celebrex, Erbitux, Herceptin, Iressa, Taxol, Velcade, TNP-470, CM101, Carboxyamido-triazole, anti-neoplastic urinary protein, Isotretionin, Interferon-alpha, Tamoxifen, Tecogalan combrestatin, Squalamine, Cyclophosphamide, Angiostatin, Platelet factor-4, Anginex, Eponemycin, Epoxomicin, Epoxy-β-aminoketone, Antiangiogenic antithrombin III, Canstatin, cartilage-derived inhibitor, CD59 complement fragment, fibronectin fragment, Gro-beta, heparinases, heparin hexasaccharide fragment, human chorinonic gonadotropin, interferon (alpha, beta or gamma), interferon inducible protein (IP-10), Interleukin-12 (IL-12), Kringle 5 (plasminogen fragment), tissue inhibitors of metalloproteinases, 2-Methoxyestradiol (Panzem), placental ribonuclease inhibitor, plasminogen activator inhibitor, Prolactin 16 kD fragment, Retinoids, Tetrahydrocortisol-S, Thrombospondin-1, Transforming growth factor beta, Vasculostatin, and Vasostatin (calreticulin fragment).

Disc cells can be transferred from another disc 100 within the patient into the shunted disc 100 to expedite disc regeneration. Gene therapy can also be done in the shunted disc 100 to promote disc regeneration.

Since cellularity within discs 100 is always low, the shunted disc 100 can be further revitalized by injection of donor cells from an external source to expedite regeneration. The avascular disc 100 is well sealed. Even small ions, such as sulfate, and small molecules, such as proline, are greatly limited from diffusing into the nucleus pulposus 128. The well-sealed disc 100 may be able to encapsulate donor cells from a disc 100 of a human cadaver without triggering an immune response. For disc 100 regeneration, the donor cells can also be stem cells, notochord or chondrocytes from tissue cultures, animals or biotechnology. Cells sensitive to sterilization can be loaded aseptically. The method for injecting donor cells into a shunted disc 100 can be done in multiple stages, separated by days, weeks, months or even years. Initial filament 126 deployment prepares the biological conditions, including pH, electrolytic balance and nutrients, to favor cell proliferation before cell injection. Donor cells can also be encapsulated within biodegradable capsules, seeded within the filament 126 and released after suitable biological conditions have been attained or achieved by the filament 126.

In recent years, cell transplants from cadavers or live donors have been successful in providing therapeutic benefits. For example, islet cells from a donor pancreas have been injected into a type I diabetic patient's portal vein leading into the liver. The islets began to function as they normally do in the pancreas by producing insulin to regulate blood sugar. However, to keep the donor cells alive, the diabetic patient requires a lifetime supply of anti-rejection medication, such as cyclosporin A. In addition to the cost of anti-rejection medication, the long-term side effects of these immuno-suppressive drugs include cancer. The benefit of cell transplants may not outweigh the potential side effects.

Both the introducer needle 381 and rotating needle 101 can be the tissue-puncturing needle. The filament-guiding device or filament guide can be the elastically curved tube 375, elastic extension arm 434 and/or elastic extension tube 435. The elastically curved tube 375 can have a window 402 and groove 405. The extension arm 434 can be tapered, with slots 438 or hole 377. The rotating device can be the spindle 390 or rotating needle 101.

It is to be understood that the present invention is by no means limited to the particular constructions disclosed herein and/or shown in the drawings, but also includes any other modification, changes or equivalents within the scope of the claims. Many features have been listed with particular configurations, curvatures, options, and embodiments. Any one or more of the features described may be added to or combined with any of the other embodiments or other standard devices to create alternate combinations and embodiments.

It should be clear to one skilled in the art that the current chemicals, biochemicals, drugs, methods, embodiments, materials, constructions, cells, tissues or puncture sites are not the only uses for which the invention may be used. Different chemicals, constructions, methods, coatings or designs for the filament 126 can be substituted and used. Nothing in the preceding description should be taken to limit the scope of the present invention. The full scope of the invention is to be determined by the appended claims.

What is claimed is:

1. A filament spooling device, comprising:
a rotating needle comprising a lumen,
a flexible filament at least partially within said lumen of said rotating needle,
a filament guide comprising a proximal end, a middle portion and a distal end,
wherein said flexible filament engages said distal end,
wherein said filament guide further comprises a first position and a second position,
wherein in said first position, said middle portion and said distal end are proximate said rotating needle,
and wherein in said second position, said middle portion is proximate said rotating needle and said distal end separates from said rotating needle, thereby said filament guide facilitates spooling of said flexible filament over said rotating needle.

2. The filament spooling device of claim 1, wherein a cross section of said rotating needle is non-round.

3. The filament spooling device of claim 1, wherein said rotating needle comprises a step.

4. The filament spooling device of claim 3, further comprising a tubular spindle sized and configured to fit said step of said rotating needle.

5. The filament spooling device of claim 4, wherein said tubular spindle has a tapered edge.

6. The filament spooling device of claim 4, wherein said tubular spindle is biodegradable.

7. The filament spooling device of claim 1, further comprising a tissue puncturing needle sized and configured to house said rotating needle and filament guide.

8. The filament spooling device of claim 1, wherein said filament guide is an elastic tube comprising an opening between said distal end and middle portion.

9. The filament spooling device of claim 8, wherein in said first position, said rotating needle is at least partially within said distal end.

10. The filament spooling device of claim 8, wherein in said second position, said rotating needle protrudes through said opening, thereby said filament guide is in a spooling position for spooling said flexible filament on said rotating needle.

11. The filament spooling device of claim 10, wherein when said filament guide is in said spooling position, said elastic tube between said distal end and middle portion is elastically curved.

12. The filament spooling device of claim 8, wherein when said rotating needle protrudes through said distal end of said elastic tube, said filament guide is in a tissue puncturing position.

13. The filament spooling device of claim 12, wherein when said filament guide is in said tissue puncturing position, said elastic tube between said distal end and middle portion is resiliently straightened.

14. The filament spooling device of claim 8, wherein said opening comprises a proximal edge and a distal edge, wherein at least one of said proximal and distal edge of said opening is beveled.

15. The filament spooling device of claim 8, wherein said distal end of said elastic tube is beveled.

16. The filament spooling device of claim 8, further comprising an extension tube located over said distal end of said elastic tube.

17. The filament spooling device of claim 16, wherein said extension tube comprises a beveled distal portion.

18. The filament spooling device of claim 1, wherein said flexible filament is a mono-filament.

19. The filament spooling device of claim 1, wherein said flexible filament is a braided filament.

20. The filament spooling device of claim 1, wherein said flexible filament is a wire.

21. The filament spooling device of claim 1, wherein said flexible filament is water permeable.

22. The filament spooling device of claim 1, wherein said flexible filament has a non-round cross-section.

23. The filament spooling device of claim 1, wherein said flexible filament has a plurality of protrusions.

24. The filament spooling device of claim 1, wherein said flexible filament has a plurality of indentations.

25. The filament spooling device of claim 1, wherein at least a portion of said flexible filament is locatable within said filament guide.

26. The filament spooling device of claim 1, further comprising an extension arm located at said distal end of said filament guide.

27. The filament spooling device of claim 26, wherein said extension arm is tapered.

28. The filament spooling device of claim 1, wherein said flexible filament is biodegradable.

29. A method of spooling a flexible filament into the wall of urethra thereby bulking the wall of urethra to treat stress incontinence, the method comprising the steps of:
(a) inserting a flexible filament in a lumen of a rotating needle;
(b) puncturing the urethra with said rotating needle;
(c) deploying a filament guide;
(d) spooling said flexible filament over at least a portion of said rotating needle into a spool;
(e) withdrawing said rotating needle;
(f) deploying said spool of flexible filament within the wall of urethra;
(g) removing said filament guide.

30. The method of claim 29, wherein step (c) is performed by partially withdrawing said rotating needle.

31. The method of claim 29, wherein said flexible filament in step (d) is spooled over a spindle.

* * * * *